United States Patent [19]

Berka et al.

[11] Patent Number: 5,360,901

[45] Date of Patent: Nov. 1, 1994

[54] GENE SEQUENCE ENCODING *ASPERGILLUS NIGER* CATALASE-R

[75] Inventors: Randy M. Berka, San Mateo; Timothy Fowler, Redwood City; Michael W. Rey, San Mateo, all of Calif.

[73] Assignee: Genencor International, Inc., Rochester, N.Y.

[21] Appl. No.: 845,989

[22] Filed: Mar. 4, 1992

[51] Int. Cl.$^5$ .................. C12N 15/53; C12N 15/80; C12N 9/08
[52] U.S. Cl. ........................... 536/23.2; 435/69.1; 435/71.1; 435/172.3; 435/192; 435/254.3; 435/320.1
[58] Field of Search ............. 435/69.1, 71.1, 172.3, 435/192, 254, 320.1, 254.3; 536/27, 23.2; 935/14, 27, 36, 56, 68

[56] References Cited

PUBLICATIONS

Gruft, et al., 1978, Can. J. Biochem., 56:916–919.
Mosavi-Movahedi, et al., 1987, Int. J. Macromol. 9:327–332.
Kikuchi-Torii, et al., J. Biochem. 92:1449–1456.
Cullen, et al., 1987, Bio/Technology 5:369–376.
Barton, et al., 1972, J. Bacteriol. 111:771–777.
Fowler, et al., 1990, Current Genetics 18:537–545.
Van Hartingsveldt, et al., 1987, Mol. Gen. Genet. 207:71–75.
Wilson, et al., 1988, Nucl. Acids Research 16:2339.

*Primary Examiner*—Robert A. Wax
*Assistant Examiner*—Rebecca Prouty
*Attorney, Agent, or Firm*—Karen I. Krupen

[57] ABSTRACT

The invention discloses the application of genetic engineering techniques to create novel strains of *A. niger* which produce high levels of catalase (catR gene product, catalase-R) while generating minimal sodium gluconate waste material.

2 Claims, 26 Drawing Sheets

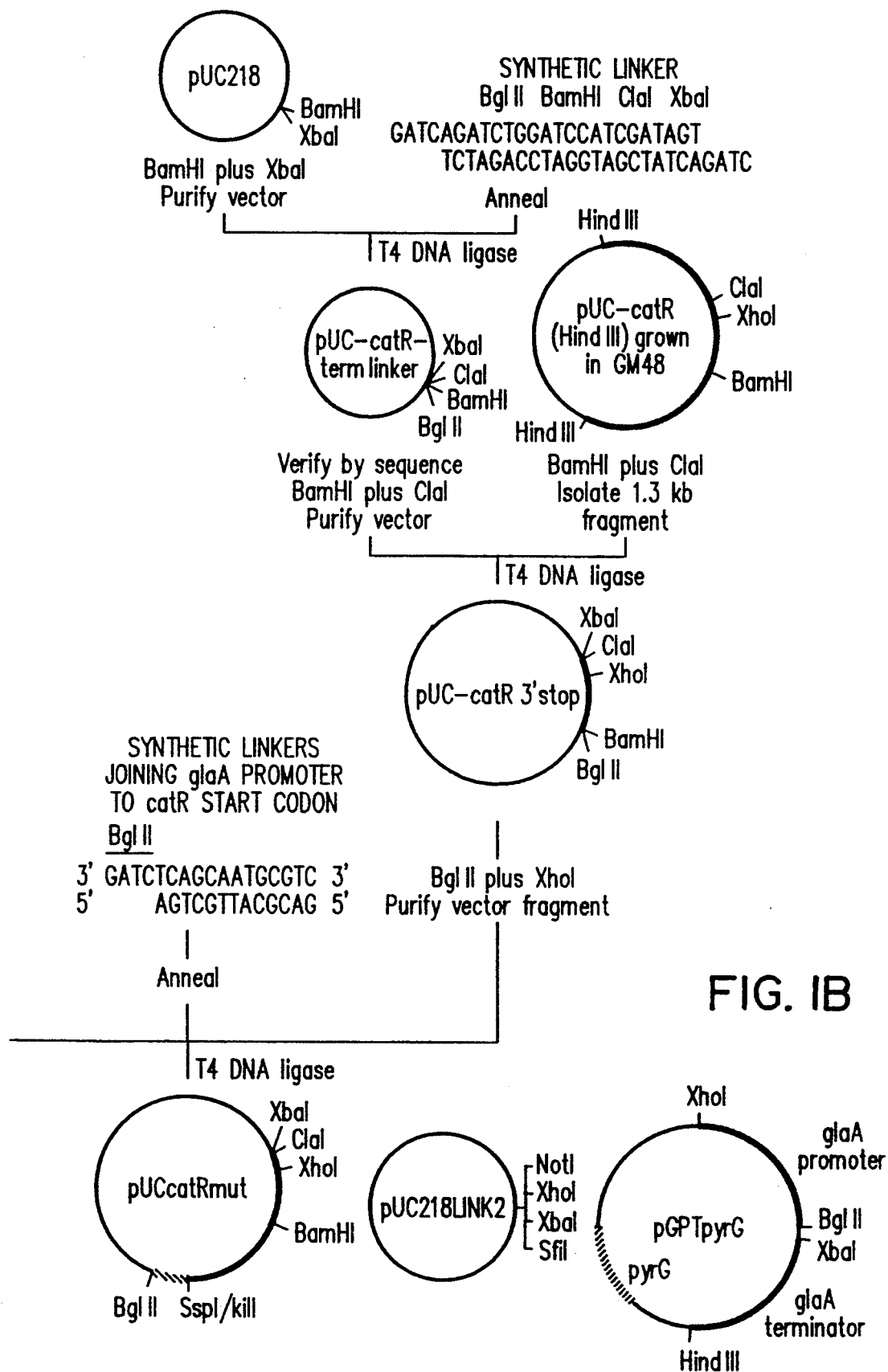
FIG. IB

| FIG. 1A | FIG. 1B |
| --- | --- |
| FIG. 1C | FIG. 1D |

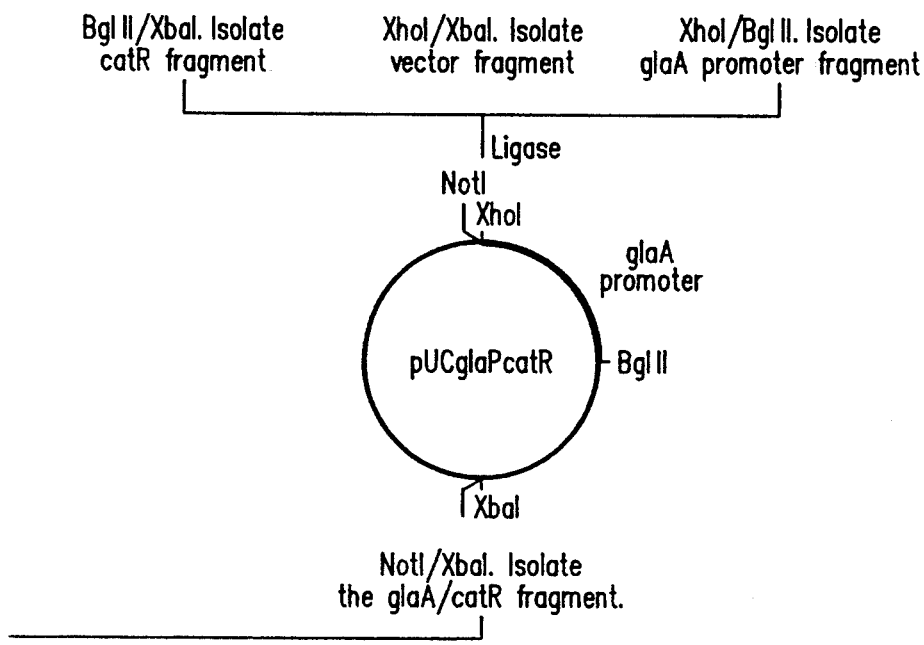
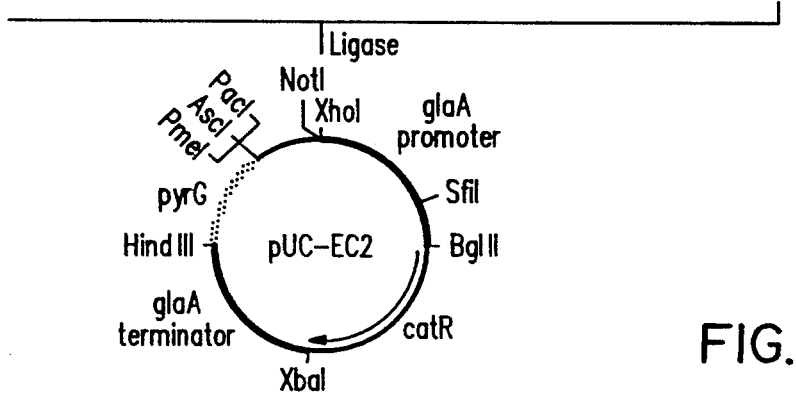
FIG. 1D

```
                                                                                                Dra III
                                                                                                 ...                        Esp3 I         Bcl I
                                                                                                 ...                         ...           ...
CTTGTCACCGAGTGCCCGTTTGTCACTTGTTGTGGTGATCTTGAGCACACATGCGTTCCTCTCGTCTCATCACATGAGTGATCAACATTG        90

Esp3 I      Acc III
                                                                   ...        ...
CATGACCCTAGTGGAGCCCCTTCGTCTCCCAACAGGAGGGTCCGGATTACCAAGTCCCGACACCGTTTGGCGTGTAATTCGACTCAAATTC      180

Mlu I
                    :.....    Eam1105 I  Hpa I              Nco I                                 Bln I
                              ....:...   :.:.               :...                                  :...
TGGATTCGTAGCTTAACTAAGACGCGTGGTCTGTTAACCGGCTCGTGTTACCGGGCTCCCCATGATGCCGATATAAGGACCCTAGGGACTCCCCCTGGTG  270

PshA I                                                                                                          Pvu II
     :...                EcoR I                                                                                      :...
     ......              :...     Bbv II
                                  ....
ACTCTCGTCGGAAGATCGCAGCACTCTGAATTCTCCTAGTCTCGTTACTCCGCCATGGTCATTTCTGCCTTTGCCAGTCGTGTTGCTG             360
                                                                 Met Arg His Phe Trp Leu Leu Pro Ala Val Ala
                                                                                        Taq II-2
                                                                                        ....

Age I
                                                                                                                              :...
GTATCGCTGGGGCTCAATGCCCCTACCTGTCGGGTGAAATGAGTTTCACCCAGGAGCAGGACAATGCTGGGATACCATTGAGGTCACGG       450
Gly Ile Ala Gly Ala Gln Cys Pro Tyr Leu Ser Gly Glu Met Ser Phe Gln Glu Gln Asp Asn Ala Gly Asp Thr Ile Glu Val Thr

AGCAGCCCATTGACAACACCCTGTATGTCAATGACACCGGTAGCTACATGACTACCGACTTTGGCACTCCGACATCCGACTCCGACCAGTC      540
Glu Gln Pro Ile Asp Asn Thr Leu Tyr Val Asn Asp Thr Gly Ser Tyr Met Thr Thr Asp Phe Gly Thr Pro Ile Ser Asp Gln Thr Ser

Bsp120 I
     :......
      Apa I              EcoN I         Eco57 I         HinD III
      :...               :...           :...            :...
TCAAGGGCGGGCCCCGTGGTCCTACCCTGTGGAGGACTTTATCTTCCGTCAGAAGCTTCAGCGGTTCGACCATGAGCGTGTAAGTACAG        630
Leu Lys Ala Gly Pro Arg Gly Pro Thr Leu Leu Glu Asp Phe Ile Phe Arg Gln Lys Leu Gln Arg Phe Asp His Glu Arg - - - - -
```

FIG. 2A'

```
                                                                                      .BstX I
                                                                                      :::
TAACTGCTGGGTGTGTAGTAACAATAAATTGACCCAGTGGTTTCAATTAGGTCCCCGAGCGGTCGTCACGCCCGTGGTGCCGGTGC    720
- - - - - - - - - - - - - - - - - - - - - - - - - - - - - - -Val Pro Glu Arg Val Val His Ala Arg Gly Ala Gly Ala

.Nde I                                  .Bsa I
:::                                     :::
ATATGGTACTTTCAAATCCTACGCCGACTGGTCGCCGAACGTCACGGCTGCCGATTTCTTGAGTGCCAACGATAAGGAGAGCCCTATGTTCTG    810
Tyr Gly Thr Phe Lys Ser Ile Ala Asp Trp Ser Asn Val Thr Ala Ala Asp Phe Leu Ser Ala Asn Asp Lys Glu Thr Pro Met Phe Cys

TGCCTTCTCTACTGCTGTGTCCGTTCCGTGGTAGTGTTGACACTGCGGCGTGATGTTCACGGTCACGCTTGTCGGTTCTCACACTGACGAGGG    900
Arg Phe Ser Thr Val Val Gly Phe Arg Gly Ser Val Asp Thr Ala Arg Asp Val His Gly His Ala Cys Arg Phe Tyr Thr Asp Glu Gly

.BstE II                    .Tth111 I
           :::                         :::
TAACTATGGTATCTTGATATGGTCACCCAACAATAATTCAATACATGTCTACTAGACATGTCGGTATCAATTCG                   990
Asn Tyr - - - - - - - - - - - - - - - - - - - - - - - - - - - - - Asp Ile Val Gly Ile Asn Phe

.Bsg I
                                                                          :::
CCCCCTTCTCATCCAGGACGCCATCCAGTTCCCCGATCTCTGTCCACGGCCATCAAGCCCATGCCCAACAATGAGATCCCCAGGCCGCTA    1080
Ala Pro Phe Phe Ile Gln Asp Ala Ile Gln Phe Pro Asp Leu Val His Ala Ile Lys Pro Met Pro Asn Asn Glu Ile Pro Gln Ala Ala

.Eco57 I
     :::
CTGCACACACTTCCGCTTGGGACTTCTTCAGCCAGGACTGCCCTCCACAGTGCCTTGTGCCTGATGTCTGGTAACGGTATTCCTC           1170
Thr Ala His Thr Ser Ala Trp Asp Phe Phe Ser Gln Ser Gln Ser Thr Ala Leu His Ser Ala Leu Trp Leu Met Ser Gly Asn Gly Ile Pro
                                                                                            ———— Peptide 1 ————

GTTCTTTCCGCCACATGAACGGCTACGGAGTCCACAGCTTCCGCTTCGTCGCTGCCAATGGCACTTCCAAGGTGGTGCCGAACACCTTGGA   1260
Arg Ser Phe Arg His Met Asn Gly Tyr Gly Val His Ser Phe Arg Phe Val Ala Ala Asn Gly Thr Ser Lys Val Val Arg Thr Pro Trp
—————————————————— Peptide 5 ——————————————————
—— Peptide 1 ——
```

```
                     .RieAI                                           .Bpu10 I                                    .Alwn I
                     : : :                                            : : :                                       : : :
AGTCCAACAGGGTGTTGCCAGTCTGGTGTGGGATGAAGCTCAGCCCGCTGCTGCTAAGAACAGTGACTACCACCGGCCAGGATCTGTACA        1350
Lys Ser Gln Gln Gly Val Ala  Ser Leu Val Ala  Ser Leu Val Trp Asp Glu Ala Gln Ala Ala Gly Lys Asn Ser Asp Tyr His Arg Gln Asp Leu Tyr
                            .BaI I                                                             .BsaB I
                            : : :                                                              :.:Cla I
ATGCGATGCCCAATGGCCACTACCCGAAATACGAGGTCAGCCAATCCCTTGATGTCTATCGATAGAGCCTTTTGCTGACAATCCCTAGG        1440
Asn Ala Met Pro Asn Gly His Tyr Pro Lys Tyr Glu ---
               .PflM I                                                       .BamH I
               :...:                                                         :...:Bsu90 I         .BstX I
                                                                             :..:..:              : : :
TCCAAGCCCCAGATCATGGATGAGGCTGACATGCTTCGTTTCGGCTTCGACCTTCTGGATCCCACCAAGTTGGTCCCCGAGGAGGTTGTCC      1530
Leu Gln Ala Gln Ile Met Asp Glu  Ala Asp Met Leu Arg Phe Gly Phe Asp Leu Leu Asp Pro Thr Lys Leu Val Pro Glu Glu Val Val
                   .Ecl136 II
                   :..:Sac I
                   :...:                                                        .Eco57 I
CTTACACTCCTCTCGGAATGATGGAGCTCAATGCCAACCCACCAACTACTTTGCTGAAGTTGAACAGGCTGGTGTGTATGTATTCCCCATT ------      1620
Pro Tyr Thr Pro Leu Gly Met Met Glu Leu Asn Ala Asn Pro Thr Asn Tyr Phe Ala Glu Val Glu Gln Ala Gly --------
                                                                   .Pst I
                                                                   : : :
CATCAAATGCCAGACATAATCTAACTTCTGCAGTTCAACCCGGTCACGTCCTGGCATTGACTTCACCGACGACCCCCTGCTGCAA           1710
------- Phe Gln Pro Gly His Val Val Pro Gly Ile Asp Phe Thr Asp Pro Leu Leu Gln
        .Esp3 I
        :..:Earn1104 I
        :....:                                                                       .PflM I
                                                                                     :...:
GGCCGTCTCTTCTCCTACCTGACACTCAGTTGACCCGTCACGGCGGTCCCAACTTCGAGCAAATCCCCGTCAACCGTCCTCGCAAGCCC      1800
Gly Arg Leu Phe Ser Tyr Leu Asp Thr Gln Leu Thr Arg His  Gly Gly Pro Asn Phe Glu Gln Ile Pro Val Asn Arg Pro Arg Lys Pro
                                                                                            .BstE II
                                                                                            : : :
GTTCACAACAACAACCGTGACGGCTTCGGCCAGCAGATCCCCACCAACAACTGGCCTACACCCCCAACAGCATGAGCAACGGTTAC         1890
Val His Asn Asn Asn Arg Asp Gly Phe Gly Gln Gln Ile  Pro Thr Asn Asn Trp Ala Tyr Thr Pro Asn Ser Met Ser Asn Gly Tyr
```

```
  .Eam1105 I
  :....: .BstX I
         :....:
CCCATGCAAGCCAACCAGACCAGGGTCATGGTTTCTTCACCGGGCCCTACGGCTTCCGGCCATCTCTGCTCCGGCCAGACCAGCCCG  1980
Pro Met Gln Ala Asn Gln Thr Gln Gly His Gly Phe Phe Thr Gly Pro Tyr Arg Ala Ser Gly His Leu Val Arg Gln Thr Ser Pro

.Eam1105 I                          .PflM I                         .Esp I
  :....:                              :....:                          :....:
ACCTTCAATGACCACTGTCCCAGCCCGGCCATGTTCTGGAACTCTCTGATCCCGCTGAGCAGCAGATGGTTGTCAACGCCATTGTCTTT  2070
Thr Phe Asn Asp His Cys Pro Gln Pro Ala Met Phe Trp Asn Ser Leu Ile Pro Leu Ser Ser Arg Trp Leu Ser Thr Pro Leu Ser Phe
                                                                                        ——— Peptide 3 ———

.Bsi I
                                                                                              :....:
                                                                                        ——— Peptide 2 ———
  .Hpa I
  :....:
GAGAACTCCAAGGTAACAGCCCCCACGTTCGGAAGAACGTTGTCAACAGCTGAACATGGTCAACAACAACCTCGCCGTCCGTGTCGCT  2160
Glu Asn Ser Lys Val Asn Ser Pro His Val Arg Lys Asn Val Arg Lys Asn Val Asn Gln Leu Asn Met Val Asn Asn Asn Leu Ala Val Arg Val  Ala
——— Peptide 2 ———

.Bsa I                                                              .Acc65 I
  :....:                                                              :....: .Kpn I
                                                                            :....:
CGTGGTCTTGGTCTCGATGAGCCCTCCGATGAGCCCTCCGATGAGCCCTCCCCAACCCGACTTACTACACCTCCAACGTCGGTACCTTCGGCAAGCCCCTC  2250
Arg Gly Leu Gly Leu Asp Glu Pro Ser Pro Asn Pro Thr Tyr Tyr Thr Thr Ser Asn Val Gly Thr Phe Gly Lys Pro Leu
```

```
                                                              Nco I
                                                              PflM I
  Bpu10 I  BspM I      Pst I                              ┊   ┊
  ┊        ┊           ┊                                  ┊   ┊
CTCAGCATCGAGGGTCGGCTTCCTGGCCTCGAACTCCCACCCGAATCCATCAAGCAGGGCCAGGCCATGGCCGCCAGTTC   2340
Leu Ser Ile Glu Gly Leu Gln Val Gly Phe Leu Ala Ser Asn Ser His Pro Glu Ser Ile Lys Gln Gly Gln Ala Met Ala Ala Gln Phe
                                  Stu I
                                  ┊
TCTGCCGCTGGCGTCGACCTGAACATTGTCACCGAGGCCTACGCCGATGTGTCAACACCACCTACGCCCTGTCTGATGCCATCGACTTT   2430
Ser Ala Ala Gly Val Asp Leu Asn Ile Val Thr Glu Ala Tyr Ala Asp Gly Val Asn Thr Thr Tyr Ala Leu Ser Asp Ala Ile Asp Phe
                      Eam1104 I
                      ┊    Bsg I
                      ┊    ┊
GACGCCCTCATCATCGCCGATGGTGTGCAGAGCCTCTTCGCCTCCCCGGCTCTCGCTAACCAGATGAACTCTACCGCCACCTCTACTCTC   2520
Asp Ala Leu Ile Ile Ala Asp Gly Val Gln Ser Leu Phe Ala Ser Pro Ala Leu Ala Asn Gln Met Asn Ser Thr Ala Thr Ser Thr Leu
                        Alwn I
                        PflM I
                        ┊
TACCCTCCTGCCAGACCTTTCCAGATCCTGGTGATTCTTTCAGGTACGGTAAGCCCGTGGCTCGTCGGCAGTGGCAGTGTTGCGCTC   2610
Tyr Pro Pro Ala Arg Pro Phe Gln Ile Leu Val Asp Ser Phe Arg Gly Lys Pro Val Ala Ala Val Gly Ser Gly Val Ala Leu
                                 Xho I
                                 Esp3 I
                                 MlaA I
                                 Sci I
                                 ┊
                                 Xcm I
                                 ┊
AAGAACGCTGGTATTGATTCCTCCCGCTCTGTGTGTACACTGGCTCGAGCCGAGACGACGGAGAAGATCGCCAAGGAGGTCTTGGAGGGA   2700
Lys Asn Ala Gly Ile Asp Ser Ser Arg Ser Val Tyr Thr Gly Ser Ser Glu Thr Thr Glu Lys Ile Ala Lys Glu Val Leu Glu Gly
```

FIG. 2C'

```
                                        .Age I
                                        :::
CTCTACACTTTCCGTTTTGTGGACCGGTTGCCGCTGGACTGAGTAAGGGTATCACGTTTGTACTGTACTCACGTTCATCGTTTGTGATGA    2790
Leu Tyr Thr Phe Arg Phe Val Asp Arg Phe Ala Leu Asp Glu
     .Cla I                                   .Bst1107 I
      :::                                      :::
TACATTGATCGATAGATATTTTGTGAGATAGATAGAGTATACTAGAGWGKACATATCTCTACTGATGAGGTGTTGTGCTGCTGCAA       2880
                 .Eam1104 I .Nhe I                           .Hpa I     .Eam1104 I    .BsaB I
                  :::        :::                              :::        :::           :::
CACATATTTATGAATATATATTCTCTTCTTTGTGAAAGCTAGCCTTCTATATAATCAGCAATGGTTAACTCTTCCAATTCTATAGATACC    2970
AATCACCTAACCCACTCGGAATGACGACAGAAAAACATCGACATGTTCGCCCAAGTAAAGCTACTTGAACTTCTACATTTATGCTATGCTG  3060
       .Gsu I
        :::
GAGTCCTCTCATAAGTCCAGAATAAACAAAGAGATCCGATCCTGCTC   3107

| FIG. 2C' | FIG. 2C" |

FIG. 3A'

GCGGCCGCCTCGAGGATTGTCTGAACATTGGACATTCGGGCGCCCAGCGAACCCCAACTGCGGACGCGAATGCCCGTGCTGTCTCGGATCT    90
⊢linker⊣                                                           ⊢———— glaA promoter ————

TTGGCGGGAGGCTTTGAACTGGTTCAAAGGCCATGTATGACGGCACAACGATGGTATCATCGTCGATAGACAAGAATATGCCTATCGTGT    180
———————————————————————————————— glaA promoter ————————————————————————————————

TTGTAGCGATGAACTATCGCGTAGGGGCTTCCGGGTTTCTGCCCCGAAAGGAGATTCTGAGGACGGGTCCGCCAACTTAGGTCTTTGAC    270
———————————————————————————————— glaA promoter ————————————————————————————————

CAAGCCCTTGCCCGCTAGTGGGTCGGCCGACAACATCGAGGCGTTTGGTGGAGACCAGAGACAAGGTGACAATCTGGGAGAATCAGCAGGGCTA    360
———————————————————————————————— glaA promoter ————————————————————————————————

TTTCTGTCTTGATCAGATGATCTGTACGACGGAAAACATCGCTTACAAGGACAAGCCCCTGTTTCGGGAGCCATCATGGACTCCGGTATGT    450
———————————————————————————————— glaA promoter ————————————————————————————————

GTTCCCGCAGACCCTGTCGACGGGGTCAAGGGATCAGCAGAAGTATATGCGGTTGTGGACTCTGCAGGCTGTTCCTCTTCCAACGACAC    540
———————————————————————————————— glaA promoter ————————————————————————————————

CCTGGCTTGTCTGCCGTGAGCTAGACTACACCGACTATCTCAATGCGGCAAACTCGTCGCCGGGATCCTAGGTTATCACCGTGGCGCTATC    630
———————————————————————————————— glaA promoter ————————————————————————————————

ATATGTGCCTCGACCAGACGGGACGGCCATTTGTCGGCGTCCCAGATTTTGGGTAAAGCAGGGAAGTATGCCGGGGTCCATTCATCGTG    720
———————————————————————————————— glaA promoter ————————————————————————————————

GGGCGACCAAGAGGATGAGGGGACCTTGTTCGCCCTTGTTTCAGTCCTTACGACGATCCGACGAGGTAGTCGACTATCTGGCCACCTACTTCT    810
———————————————————————————————— glaA promoter ————————————————————————————————

FIG. 3A

```
TCTATGACGCTAGCCAGGAGCAGCTTGAAGAATTAGTGGCCCTGTACCCAGAGACACCACCACATATGGGTCTCCCTTCAGGACGGGCAGGC    900
————————————— glaA promoter —————————————

CAACAACTGGTATCCGCAATTTAAGCGATTGGCCCGCCATTCTCGGCGACTTGGTCTTCACCATTACCCGGCGGCATTCCTGTCATATGCA    990
————————————— glaA promoter —————————————

GAGGAGCTCTCCCTGACCTCCCGAAATGTCGTGACCTGGGACCTATGCAGCTATGGACTATGGCAGCCAATTCTGGGACCTTCCATGGAAGTGACC   1080
————————————— glaA promoter —————————————

TGCTGCAGGTGTTCTATGGATCAAGCCGAACTATGCAGCGAGTTCCAGCCACGAGTATTATCTGAGTTTTGTATACACGCTGGATCCGA   1170
————————————— glaA promoter —————————————

ACTCCAATCGGGGAGTACATGGAATGCCCCAGTGGCAGCCGACAGTTGATGAATTCGGAGCGAACACAGTCTCCTTACGGATGAT   1260
————————————— glaA promoter —————————————

TTCCGCAACGGGACATATGAGTTCATCCTGCAGAATACCCGGCGTTCCACATCTGATGCCATTCGGGAGGGGTCCCGAGGTCAGGGACT   1350
————————————— glaA promoter —————————————

AGCCCTTATGAACGTAATGATGGAAGTGTCTGCCCTCCGGCAAAGGATATATAGGGTCATAATAAGTAGTACTAGTTATATTAATGAAGGG   1440
————————————— glaA promoter —————————————

TATATACCACGCGTTGGACCTTGGGACCTGCATTATAGCTTCCCGTTAGGTATAATTACCGTTGTTATAGCAGCCAATCAAGCCACCACG   1530
————————————— glaA promoter —————————————

CTCGACCGGGGACGGGCGAATCCCCGGGAATTGCAATTGAAATAAATTCAGGTCAATGCCGCCAGGCGATTGGACACATCTCCAAGGCACA   1620
————————————— glaA promoter —————————————
```

FIG. 3B'

GGGCCATTCTGCAGTGCCGGGGATTCAGTGCATTCCCCCGGGGCCCGGGCCCGACACGCGATAGGCTGGTTCTTCCACACCACCGGAGATTC — 1710

GTCGTTCTGAAGAGCTGAAGTGGCGAGATGGTCTCTGCAGGAATTCAAGCTAGATGCTAAGCGATATTGCATGGCAATATGTGTTGATGC — 1800
————— glaA promoter —————

ATGTGCTTCTTCCCTTCAGCTTCCCCTCGTGCAGATGAAGCTTGGCTATAAATTGAAGTGGTTGGTCGGGGTTCCGTGAGGGGCTGAAG — 1890
————— glaA promoter —————

TGCTTCCTCCCCTTTAGACGCAACTGAGAGCCTGAGCTTCATCCCCAGCATCATTAGATCTCAGCAATGCGTCATTTCTGGCTTTTGCTG — 1980
————— glaA promoter ————— | ————— catR coding region —————

CTGTTGCTGCTATGCGCTGGCTCAATGCCCCTACTGTCGGGTGAAATGAGTTTCACCCCAGGAGCAGGACAATGCTGGCGATACCATTGAGG — 2070
————— catR coding region —————

TCACGGAGCAGCCCATTGACAACACCCTGTATGTCAATGACACCGTAGCTACACGACTACCGACTTGGCCACTCCGACTCTCCGACCAGA — 2160
————— catR coding region —————

CCAGTCTCAAGGCCGGGCCCCGTGTCCTACCCTGTTGGAGGACTTATCTCCGTCAGAAGCTTCAGCGGTTCGACCATGAGCGTGTAA — 2250
————— catR coding region —————

GTACAGTAACTGCTGCGGTGTGTAGTAACAATAAATTGACCTGGTTTTCAATTAGGTCCCCGAGCCCGTCGTCCACGCCCGTGGTGC — 2340
————— catR coding region —————

CGGTGCATATGGTACTTTCAAATCCTACGCCGACTGGTCGAACGTCACGGCTGCCGATTTCTTGAGTGCCAACGATAAGGAGACCCCTAT — 2430
————— catR coding region —————

GTTCTGTCGGCTTCTCTACTGTGGTCGGTTTCCGTGTAGTGTTGACACTGCGGCTGATGTTCACGGTCACGCTTGTCGGTTCTACACTGA 2520
———— catR coding region ————

CGAGGGTAACTATGGTATCTTGATATGGTCACCCAACAATAATTCAATACATGTCTAACAGATATGTCTCTACTAGACATCGTCGGTATCA 2610
———— catR coding region ————

ATTTCGGCCCCTTCTTCATCCAGGACGCCATCCAGTTCCCCGATCTTGTCCACGCCATCAAGCCCATGCCCAACAATGAGATCCCCCAGG 2700
———— catR coding region ————

CCGCTACTGCACACTTCCGCCTTGGGACTTCTTCAGCCAGCAGAGCACTGCCCCTCCACAGTGCCTTGTGGCTAACGTGCTGATGTCTGGTAACGGTA 2790
———— catR coding region ————

TTCCTCGTTCTTTCCGCCACATGAACGGCTACGGAGTCCAGCTCAAGCTTCGCTTCGCTGCCAATGGCACTTCCAAGGTGGTGCGAACAC 2880
———— catR coding region ————

CTTGGAAGTCCAACAGGGTGTTGCCAGTCTGGTGTGGGATGAAGCTCAGCCCGCTGCTGGTAAGAACAGTGACTACCACCGCCAGGATC 2970
———— catR coding region ————

TGTACAATGCGATGCCCAATGGCCACTACCCGAAATACGAGGTCAGCCAATCCCTTGATGTCTATGATAGAGCCTTTTGCTGACAATCC 3060
———— catR coding region ————

CCTAGCTCCAAGCCCAGATCATGATGAGGCTGACATGCTTCGTTCGGCTTCGACCTTCTGGATCCCACCAAGTTGGTCCCCGAGGAGG 3150
———— catR coding region ————

TTGTCCCTTACACTCCTCTCCGGAATGATGAGCTCAATGCCAACCCCACCAACTACTTTGCTGAAGTTGAACAGGCTGGTGTATGTATTC 3240
———— catR coding region ————

FIG. 3B"

| FIG. 3B' |
| FIG. 3B" |

CCCATTCATCAAATGCCAGACATAATCTAACTTCTGCAGTTCCAACCGGTCACGTCGTTCCTGGCATTGACTTCACCGACGACCCCTG  3330
———— catR coding region ————

CTGCAAGGCCGTCTCTTCTCCTACCTCGACACTCGAGTTCAGTTGACCCGGTCACCCGGCGGTCCCAACTTCGAGCAAATCCCCGTCAACCGTCCTCGC  3420
———— catR coding region ————

AAGCCCGTTCACAACAACAACCGTGACGGCTTCGGCCAGCAGCAGATCCCCACCAACAACAACTGGGCCTACACCCCCAACAGCATGAGCAAC  3510
———— catR coding region ————

GGTTACCCCATGCAAGCCAACCAGACCCAGGGTCATGGTTCTTCCACGCGCCCCTACGGCCTTCCGGGCCATCTCGTCCGCCCAGACC  3600
———— catR coding region ————

AGCCCGACCTTCAATGACCACTGGTCCCAGCCCGGCCATGTTCTGGAACTCTCTGATCCCCGCTGAGCAGCAGATGGTTGTCAACGCCATT  3690
———— catR coding region ————

GTCTTTGAGAACTCCAAGGTTAACAGAGCCCCACGTTCGGAAGAACGTTGTCAACCAGCTGAACATGGTCAACAACAACCTCGCCGTCCGT  3780
———— catR coding region ————

GTCGCTCGTGGTCTTGGTCTCGATGAGCCCTCCCCCAACCTCTCCCAACAGACCTCCAACGTCGGTACCTTCGGCAAG  3870
———— catR coding region ————

CCCCTCCTCAGCATCGAGGGTCTGCGAGGTCGGCTTCCTGGCCTCGAACTCCCACCCCGAATCCATCAAGCAGGGGCCAGGCCATGGCCGGC  3960
———— catR coding region ————

AGTTCTCTGCCGCTGGCCGTGACCTGAACATTGTCACCGGATGGTGTCAACACCACTACGCCCTGTCTGATGCCATCG  4050
———— catR coding region ————

FIG. 3C

| | |
|---|---|
| FIG. 3C' | FIG. 3C" |

FIG. 3C

ACTTTGACGCCCTCATCATCGCCGATGTGTGCAGAGCCTCTTGCCTCTCCCCGCTCTGCTAACCAGATGAACTCTACCGCCACCTCTA  4140
———————————————— catR coding region ————————————————

CTCTCTACCCTCCTGCCAGATCCTTTCCAGATCCTCGGTCGATTCTTTCAGGTACGGTAAGCCCCGTGGCTGCTGTCGGCAGTGGCAGTGTTG  4230
———————————————— catR coding region ————————————————

CGCTCAAGAACCCTGGTATTGATTCCTCCCGCTCTGGTGTGTACACTGGCTCGAGCGAGCAGCGGAGAAGATCGCCAAGGAGGTCTTGG  4320
———————————————— catR coding region ————————————————

AGGGACTCTACACTTTCCGTTTGTGGACGGGTTTGCGCTGGATGAGTAAGGTATCACGTTTGTACTTGTACTCACGTTCATCGTTTGT  4410
———— catR coding region ————————|———— catR 3' non coding DNA ————

GATGATACATTGATTGATCGATAGTCTAGAGTCGACCGCCGACCGGTGACCGACACCTGGCCGGTAGACTATTATTCCTGTTGATATGAAGG  4500
—catR 3' non coding DNA —|— linker —|———— glaA poly adenylation & termination signals ————

ATGAGCATGAGGGTAATTGCTCATATAATCATGTATGTAGTGATGTGCATAAGAGCAACGAAATGAAGCCTGATCATGTGATTGTATT  4590
———————————————— glaA poly adenylation & termination signals ————————————————

GCGACCGACGGAGAAATTGAGGATATGCGGAGATACGGACAGTGCCAGAGCCATTGTCTTCACGTAAAGTACCAGACGGTCCCTGATTTCTT  4680
———————————————— glaA poly adenylation & termination signals ————————————————

CTTGCACATAGCATTAGGCAATTGACATGTTGTCGCTCTACTGATATCACTGTCCCTCAAAGCATAGCCATGAGCTCATCTTAGATCCAA  4770
———————————————— glaA poly adenylation & termination signals ————————————————

GCACGTAATTCCATAGCCGAGGTCCACAGTGAGCAACAGCAGCATCCATCATTGCTTCTCTCCCCCAGGGGCCCTCTTAGCGACTAAACCTG  4860
———————————————— glaA poly adenylation & termination signals ————————————————

FIG. 3D'

```
GAGTATGTCTCAACCAGCCAATGAATCGTCTTCGCTTCAATGTCCTTGAGACACTTCTGAGAGGGTCCCCATCCCTCAATGCTCTAATTCAAAA    4950
——————— glaA poly adenylation & termination signals ———————
TATAGCCGAGATGCATGGTGGAGTCCAAAGTCCAAATGAGACAGTAGACAGTATTGCCGAATGACGGGGCCAGTTGCCGCGAGGTCATTGGCCGGCTGTGATG    5040
——————— glaA poly adenylation & termination signals ———————
CCATCTCGCCACTAAATCCGATCATTGATCCACCGCCCACGAGGGCCCGTCTTTGCTTTTGCCTGGCTCCAGGTTCACACATCTCTCTCTC    5130
——————— glaA poly adenylation & termination signals ———————
TGCAGCTCCAGACTGACCAGACTATTCTACTTGGTCTGATCGGCCTCCATCAGAGTCATATGGCGTTATCCCGTGCCGTTGCTGCCCAT    5220
——————— glaA poly adenylation & termination signals ———————
CGCTATCTTGATGCCGAGCTCGAACTCACTTCTTGTTTTAATAGTTGTTCTCGGTGACTGAGTGTCGGTGAGTGACAGACCACACAACACCA    5310
——————— glaA poly adenylation & termination signals ———————
TTGTTGCAGGGGGTAAATTTATTCAATTCAGGAATTGGATTGTTCGTCCCGCCATGATGTTCTTGCCGCCTTTGTTGCCCTGTTGTCG    5400
——————— glaA poly adenylation & termination signals ———————
GATGCGGACGCCCTCGCTGTGCAGCAGGCAGGTACTGCTGGATGATGAGCCGTCGGTCTCCGGGCGTCTCCGGGCCAAGCCTAACTTCCTCTTCATTCTT    5490
——————— glaA poly adenylation & termination signals ———————
ACGGATGATCAGGATCTGCAGATCGAATTCCACCGGCGTATATCCGTATACACAGGCGAGAATCAAGGAGAAGGGTACTGAGTTTTGAA    5580
——————— glaA poly adenylation & termination signals ———————
TCATTTGTTACTACTGGCCTCTGTCGTGTCCGCTCGAGTCTTTGGACCGAAGACACAGGCTCATAATACTAATGTGACGGATGTGAAC    5670
——————— glaA poly adenylation & termination signals ———————
```

FIG. 3D"

```
CCGGCCTTATGGTATGAATACCTCTCAGATCGGTCATGTTTCTTCGGTGTAAAATTGCTAATGCAGCATAGCCCGATACCCCAAGTTCGTC    5760
                    ———— glaA poly adenylation & termination signals ————
GCCCAAGGCTTCAACGCGAAAACTTCCTCCCGTTGGCTGCAGTCCCGGTTACAATACCTTCTACACGGGGAAACTGTTCAACTGCCAC        5850
                    ———— glaA poly adenylation & termination signals ————
AGGGTCGCTACCTATAATGCACCGTTTGTGAACGGCTTCAATGGCTCTGATTTCCTCCTCGATCCCCACACCTATTCCTACTGGAACGCG     5940
                    ———— glaA poly adenylation & termination signals ————
ACGTACCAACGAAACCATGAGCCTCCGCGGCGAGGACGAGCTACGAGGACAATACAACGATGTGATGCGGGAGAAGGCATCGGGTTGTTGGCA   6030
                    ———— glaA poly adenylation & termination signals ————
GATGCGCTGGACAGGACGCGCCGTTCTCGACGGTGCCTATCCGCCGCACGAACATCGATAAGCTTATCACGGTCCCTTATCAGCCA          6120
                    ———— glaA poly adenylation & termination signals ————            ┬
CCCGTCGCCATTTGCTCTACGCCAAGAGTTACAGGACTACTTCGCAGCCTGCTTATCTGCATCAAATCGTCGTACCCATTAATCCC           6210
                                                                              ——— pyrG gene ———
GTGCCACCCTATAATAGCCTGCAGGATCAATACGTTTTGACATCCGATGCCGCAGTCTGCGACTACCGTGCTGCGACATTAGTTGTATGC     6300
                                          ——— pyrG gene ———
GTATCGTAGCCGCAAGTTGCATTTCTATATCATTCATAACCATCAAAACTTTTTTCCTCATTTTATAGTATTAGTTTCCCGCGACACGGG      6390
                                  ——— pyrG gene ———
CCAGGTACGCCTCCCAACCTTCCTTCTGTACTGTTGCCGCAGCCTGCACCGGGTCCGGCCGCGGCGTAGATACCGCGACCCGCGATAATGA    6480
                                  ——— pyrG gene ———
```

| FIG. 3D' |
|----------|
| FIG. 3D" |

```
AGTCAGCACCCCGACCGATAGCCGATGCGGAGTCTGGTACTGCTGACCGAGCTTATCTCCCTTGGACGAAATGTTCACACCAGTCGTGA         6570
                     ———————— pyrG gene ————————
AGACCACAAAGTCCTCTCATCCGAAGGAGAGCTGACTTCCGACTGCACCTCACCCAAGCGAGCGGGTCGACACAAATCCCATGACGAAGT         6660
                     ———————— pyrG gene ————————
TCTTGTATTTCCGGGCATAATCAACCGAAGAAGTAGTGTACTGGCCCGGTGCCCAAGGAACCCTTAGAGGTCATTTCCGCCAAGATCAACA        6750
                     ———————— pyrG gene ————————
GACCACGTTCGGGCCCGTAGGAGAAGTCGGTGCAGACGCCGTCTGAGCCGAGAGCCTCGACGATACCCTCGCCAGGCAGGATGCTGCAGT         6840
                     ———————— pyrG gene ————————
TGATGATATGGGCCCATTCTGAGATGCGGAGACCGGAGGGTACCACGGTGGTATTGCTTCTGGACAGTGTTGCCAATGTCGATGAATTGCGGTCCT   6930
                     ———————— pyrG gene ————————
CGAAGATGAGGAAGTTGTGCTTCTGCGCAAGAGCCTTGAGGCCCTCAATGTCTCGTCGCTGAAGTCAGAGAGGATATCGATGTGCGGTTT         7020
                     ———————— pyrG gene ————————
TGATCACGGCGATGAGGACCGAGACCTCAGTGCCGTATCACCGTTAATAAGTTTGTATGCAGCATAAACAGGCAGAATGGCGGGTCGG          7110
                     ———————— pyrG gene ————————
CCTACGGGTCAGCAAGATCTAGTAGCTCCTTAGTGGTGTAACGTCGGCAGAGACGGTCACATTGGTCTTCTTGGCCCTCAGCAATTTCGAA        7200
                     ———————— pyrG gene ————————
CAGCCCGCTTGGCCAGAGCATTGGGGTGCTTGCTGGCACGGGCAGTGTAGGTCAATTGCGACTTGGAGGACATGGTGTCGGTGGAGGGGTT       7290
                     ———————— pyrG gene ————————
```

```
AATGCGGGGATGAAAGAGGCTTGTGCAATATGAGTAGCTTGGAGTTTCGACTGATAGGCCCTAATTGGTAGATCCAGAGATGCGCAAATA    7380
                                                  ——— pyrG gene ———

CTACCGAATAATTTAGCAGCGACTGGCCCCTTATATGAGGTGAACAATGCACATTCAATGTCGAGCAAAAGAGGAGCTCAGTAAATCATCG    7470
——— pyrG gene ———

CGACCCTCCACGCACCAGCCACATCGGGGTGATTTCGCCGCCTCCCGGAACCGTGGGGTTCAGCCACACCTGCAAAGGCAGTTCCTTT    7560
——— pyrG gene ———

CCATTGAAGTTGCCACACCCAGGTTCATTGGAGCTCGTCGTATTTTCCCTGCTGCACATGGGGAAATAGACCAGCTCAATCAGAAAGCCATT    7650
——— pyrG gene ———

GTCATTCCCGACCCTAGCAGTACGCCATAGTAAACGCGTCTGTGGAGTAGTAATATACAAGTGAGAAATTTATTACATATAGCGTGGTATAG    7740
——— pyrG gene ———

CCAACAGCGCCAATCACACCTGACGGAAGTCAATCCAAACTTTAAAAGGTAGGGAAATCAACTCCCTCGCGACTTCCAAAAGAGGTCAAT    7830
——— pyrG gene ———

CCCCAAAGAGCTCCCTGTGCAAGCAAGTAGAAGCTGCCGGACCGGACCGACCCCGGCTTGCCGGAGTACACGTATCCGTAAAGGAAC    7920
——— pyrG gene ———

AGTGAGCGACCGAGAACCCAAATGCTTCCAAGGCCAGTTGCCAACTGGGGTACTTCAATCCAGCCACCAGGATGAAGAGCATAGTTTGG    8010
——— pyrG gene ———

CTGGAGTTCTCAAGGAAGTTGGCATGAGCGTGAGCGTAACTGCTCAGCCTTGGGCTGCACGATTGGAATGTATGTTAGCTCGAGGAA    8100
——— pyrG gene ———
```

FIG. 3E

| FIG. 3E' |
| FIG. 3E" |

FIG. 3E

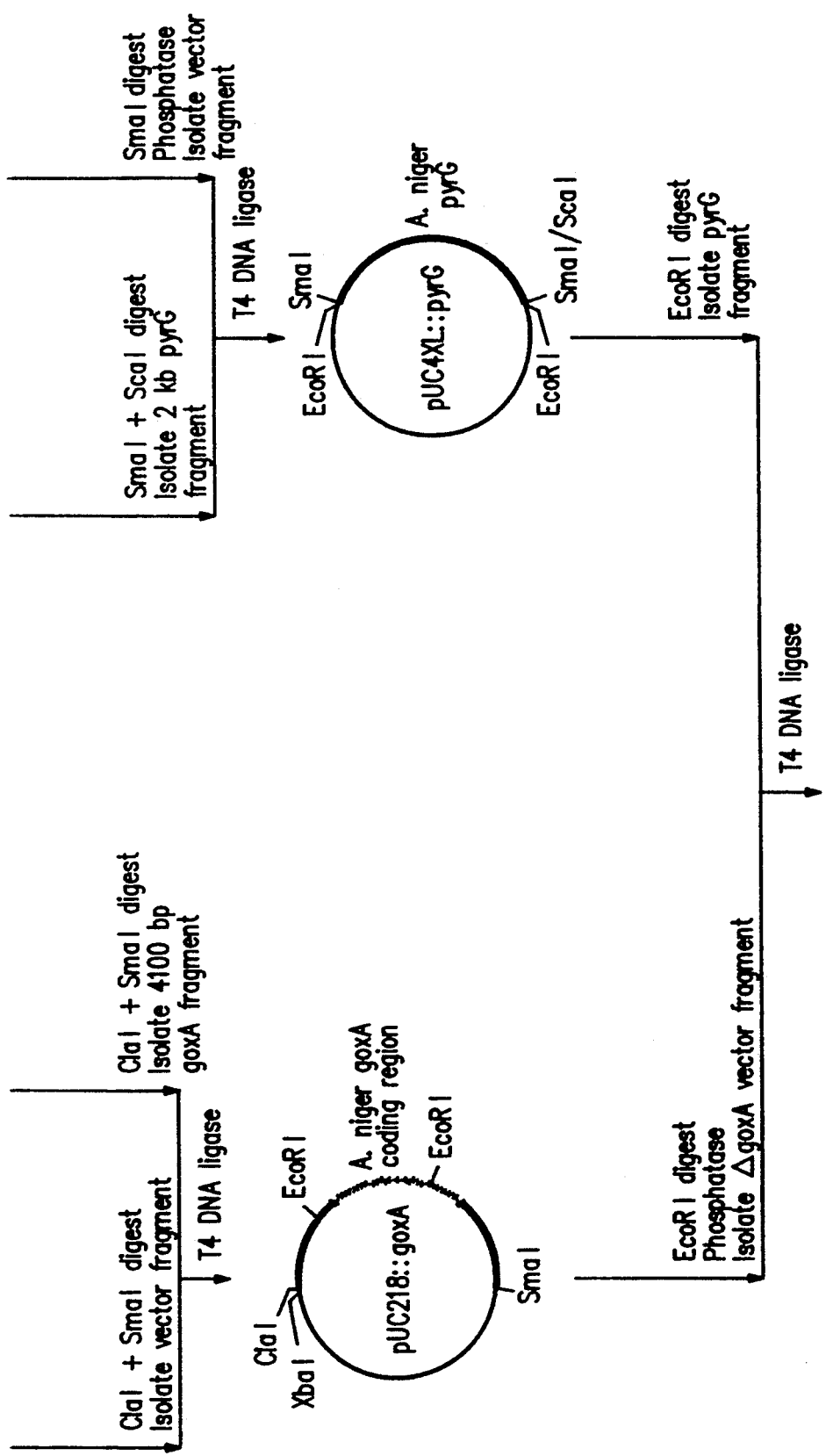
FIG. 4A"

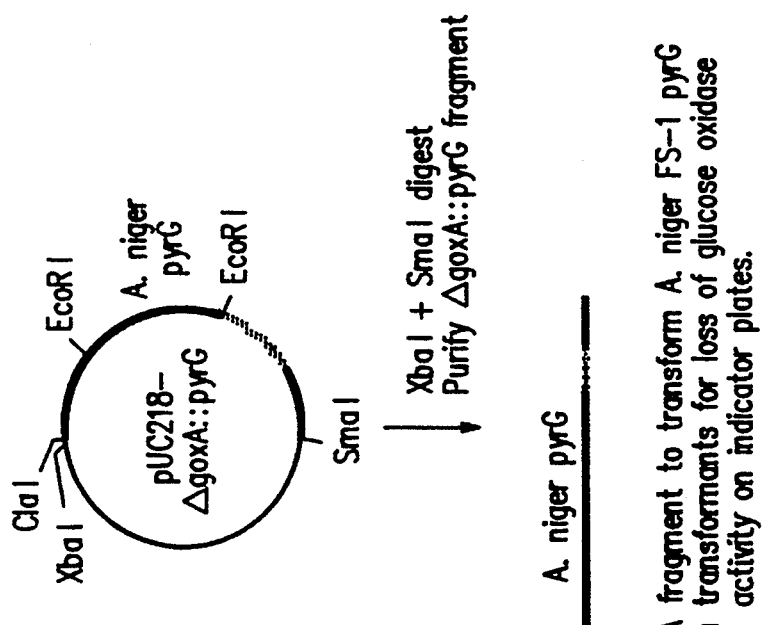
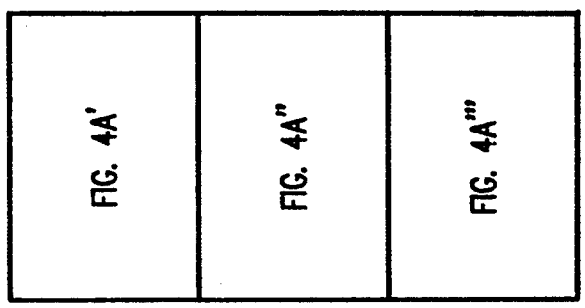
FIG. 4A'''
FIG. 4A

GENE SEQUENCE ENCODING *ASPERGILLUS NIGER* CATALASE-R

FIELD OF THE INVENTION

The invention relates to the application of genetic engineering techniques to create novel strains of *A. niger* which produce high levels of an endogenous catalase enzyme (catR gene product, catalase-R) while generating minimal sodium gluconate waste material. Specifically, high levels of catalase-R are generated through replacement of the endogenous catR gene promoter with the *A. niger* glucoamylase (glaA) gene promoter which results in not only higher levels of catalase-R, but also eliminates the requirement for hydrogen peroxide to act as an inducer for catalase synthesis, and deletion of the endogenous glucose oxidase (goxA) gene greatly reduces the level of sodium gluconate waste product, thereby minimizing the need for expensive waste handling.

BACKGROUND OF THE INVENTION

Catalases [hydrogen peroxide: hydrogen peroxide oxidoreductases (EC 1.11.1.6)] are enzymes which catalyze the conversion of hydrogen peroxide ($H_2O_2$) to oxygen ($O_2$) and water ($H_2O$) according to the following formula:

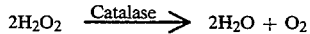

$$2H_2O_2 \xrightarrow{\text{Catalase}} 2H_2O + O_2$$

These ubiquitous enzymes have been purified from a variety of animal tissues, plants and microorganisms (Chance and Maehly 1955 Methods Enzymol. 2: 764–791; Jones and Wilson 1978 in H. Sigel (ed.), *Metal Ions in Biological Systems*, Vol. 7, Marcel Dekker Inc., New York). Nearly all forms of the enzyme which have been characterized consist of four polypeptide subunits, each having a molecular weight of 50,000 to 60,000 and containing one protohemin prosthetic group per subunit (Wasserman and Hultin 1981 Arch. Biochem. Biophys. 212: 385–392; Hartig and Ruis 1986 Eur. J. Biochem. 160: 487–490). Bovine liver catalase has been the most extensively studied variety of this enzyme [Schonbaum and Change 1976 in *The Enzymes* (P. D. Boyer, ed.) 3rd edn., vol. 13, pp. 363–408, Academic Press, New York]. The complete amino acid sequence and three dimensional structure of bovine liver catalase are known (Schroeder, et al., 1982 Arch. Biochem. Biophys. 214: 397–412; Murphy, et al., 1981 J. Mol. Biol. 152: 465–499).

Although less well-studied from a biochemical and biophysical standpoint, catalases from filamentous fungi have several characteristics that distinguish them from their mammalian counterparts. While similar in subunit number and heme content, fungal catalases are substantially larger molecules than those from other organisms, having subunit molecular weights ranging from 80,000 to 97,000 (Vainshtein, et al., 1986 J. Mol. Biol. 188: 63–72; Jacob and Orme-Johnson 1979 Biochem. 18: 2967–2975; Jones, et al., 1987 Biochim. Biophys. Acta 913: 395–398). More importantly, catalases from fungi such as *Aspergillus niger* are more stable than beef liver catalase to proteolysis and to inactivation by glutaraldehyde, SDS, and have lower affinity for catalase inhibitors such as cyanide, azide and fluoride (Wasserman and Hultin 1981 Arch. Biochem. Biophys. 212: 385–392). In addition, *A. niger* catalase is significantly more stable than beef liver catalase when subjected to extremes of pH, hydrogen peroxide, and temperature (Scott and Hammer 1960 Enzymologia 22: 229–237). Although fungal catalases offer stability advantages, the corresponding mammalian enzymes such as beef liver catalase appear to have higher catalytic activity (Gruft, et al., 1978; Kikuchi-Torii, et al., 1982). However, since enzyme stability is an important factor in the biotechnological utilization of enzymes, there has been considerable interest in the use of fungal catalases, especially for applications involving neutralization of high concentrations of hydrogen peroxide. Vasudevan and Weiland (1990 Biotechnol. Bioeng. 36: 783–789) observed that the rate of deactivation in $H_2O_2$ was at least an order of magnitude lower for *A. niger* catalase than for beef liver catalase. The differences in stability of these two enzymes can probably be attributed to differences in structural characteristics and composition of the proteins [Vasudevan and Weiland 1990 Biotechnol. Bioeng. 36: 783–789].

Catalase preparations from *A. niger* are sold commercially for diagnostic enzyme kits, for the enzymatic production of sodium gluconate from glucose, for the neutralization of $H_2O_2$ waste, and for the removal of $H_2O_2$ and/or generation of $O_2$ in foods and beverages. Traditionally, beef liver catalase has been the preferred enzyme for diagnostic purposes and for pharmaceutical-related applications (e.g., contact-lens cleaning/disinfection/$H_2O_2$ neutralization). However, recent outbreaks of a slow-virus disease known as BSE (bovine spongiform encephalopathy) in European cattle herds and fear that this disease might be spread to man [Dealler and Lacey 1991 Nutr. Health (Bicester) 7: 117–134; Dealler and Lacey 1990 Food Microbiol. 7: 253–280] have aroused interests in finding alternatives to beef liver catalase for most industrial applications.

Little information has been published regarding the regulation of catalase synthesis in *A. niger*. However, it has been observed that catalase is produced in response to the generation of $H_2O_2$ during growth of the organism on glucose or fatty acids. For example, during the metabolism of glucose, $H_2O_2$ is formed by oxidation of the sugar to give gluconate. This reaction is catalyzed by the enzyme glucose oxidase:

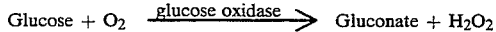

$$\text{Glucose} + O_2 \xrightarrow{\text{glucose oxidase}} \text{Gluconate} + H_2O_2$$

Cellular metabolism of fatty acids, which occurs in specialized organelles known as peroxisomes, also yields $H_2O_2$ which induces the formation of catalase. However, in a distantly related fungus (yeast), *Saccharomyces cerevisiae*, a specific catalase is induced during growth on fatty acids. This catalase, termed catalase-A (atypical), is localized chiefly in peroxisomes where fatty acid oxidation occurs. A second *S. cerevisiae* enzyme, catalase-T (typical) is a soluble cytoplasmic enzyme which is synthesized in response to a variety of other metabolic and environmental stresses. These two yeast catalases are the products of two different nuclear genes, designated CTA1 and CTT1. Similarly, two catalase genes have been isolated from *A. niger* (Genencor International, Inc., unpublished). The *A. niger* catA gene, cloned by cross-hybridization to the yeast CTA1 gene, encodes a catalase enzyme which is induced primarily during growth on fatty acids and is presumably peroxisomal. This enzyme (catalase-A) is not of commercial importance at this time, however, a second cloned *A. niger* catalase gene, designated as catR, encodes a soluble cytoplasmic enzyme (catalase-R) which represents the major activity in commercial catalase preparations.

Because of the obvious commercial interest in *A. niger* catalases, it would be desirable to obtain *A. niger* strains which produce increased levels of the catR gene product. Furthermore, it would be a significant advantage to effect high levels of catalase synthesis without the need to generate hydrogen peroxide as an inducer. Concomitant with the generation of hydrogen peroxide is the formation of sodium gluconate which represents a waste disposal problem. Thus, it is also highly desirable to minimize the production of gluconate in large scale fermentations with catalase production strains of *A. niger*. This invention discloses a solution for simultaneously accomplishing all of these objectives.

SUMMARY OF THE INVENTION

It has been discovered that it is possible to increase the expression of catalase-R (catR gene product) without the need to supply hydrogen peroxide as an inducer of catalase synthesis. Simultaneously, it was discovered that elimination of glucose oxidase gene expression (by goxA gene deletion) minimizes the generation of gluconate waste material, thereby circumventing the need for expensive waste treatment processes.

The invention includes a gene encoding *Aspergillus niger* catalase-R (catR gene) to which promoter and terminator elements of the *A. niger* glucoamylase (glaA) gene were functionally attached. Concomitantly, the coding region of the *A. niger* glucose oxidase (goxA) gene was destroyed using a targeted gene replacement strategy. The invention also includes a transformed *A. niger* organism which is capable of expressing high levels of catalase-R without hydrogen peroxide induction. This organism contains a functional expression unit comprising the catR gene, to which the *A. niger* glaA gene promoter and terminator sequences have been functionally attached.

The inventors also disclose a method for producing high levels of catalase-R comprising growth of transformed *A. niger* cells which contain chromosomally integrated copes of the catR gene under operational control of the *A. niger* glaA promoter.

FIGURES

FIG. 1 is a diagrammatic representation of the construction of the catR expression plasmid which contains the *A. niger* glaA promoter, catR coding region, glaA terminator and *A. niger* pyrG gene. A linear fragment (EC2L) containing these components was excised by digestion with NotI and PmeI and used to transform the host strain *A. niger* ΔgoxA pyrG metC.

FIG. 2 (SEQ ID NOS:4 and 5) shows the nucleotide sequence and deduced amino acid sequence of the *A. niger* catR gene and flanking regions. Restriction sites for enzymes recognizing hexanucleotide and octanucleotide sequences are shown. Introns are denoted by dashed lines. Deduced amino acid sequences corresponding to peptides sequences directly from the catalase-R protein are underlined with a solid bar.

FIG. 3 (SEQ ID NO:6) is the complete nucleotide sequence of the linear fragment (EC2L) used to transform *A. niger* ΔgoxA pyrG metC.

FIG. 4, Panel A is a diagrammatic representation of the construction of the *A. niger* vector for deletion of the glucose oxidase (goxA) gene. A linear fragment comprising the SmaI-ClaI segment was excised and used to transform the host strain *A. niger* pyrG. Panel B is a schematic showing the expected integration event at the goxA locus which results in replacement of the goxA coding region with the *A. niger* pyrG gene.

FIG. 5 is a graph showing catalase production among strains of *A. niger* ΔgoxA pyrG metC transformed with the catR expression cassette (EC2L). The original parent strain, *A. niger* FS-1, and the host strain *A. niger* ΔgoxA pyrG metC are included as controls. Each strain was grown in duplicate and the assay results from each are shown.

DESCRIPTION OF THE PREFERRED EMBODIMENTS

The details of the catR expression vector construction and genetic modifications used to derive improved catalase production strains are described. One skilled in the art will understand that various changes in the following examples could be made. Accordingly, the examples are not intended to be limiting.

The techniques used in closing the *A. niger* catR gene and construction of the catR expression cassette are conventional techniques described in Sambrook, et al., 1989 *Molecular Cloning, A Laboratory Manual*, Cold Spring Harbor Press, Cold Spring Harbor, N.Y.

1. Cloning and Characterization of the *A. niger* catR Gene

Purified catalase-R was obtained from a commercial preparation of *A. niger* catalase (Fermcolase 1000, Genencor International, Inc.) and a series of proteolytic fragments were generated. These peptide fragments were subjected to amino acid sequence analysis. The amino acid sequence information was employed to design synthetic DNA probes for identification of catR-specific cDNA sequences contained within a λgt11 library. Briefly, the peptide fragment Met-Phe-Trp-Asn-Ser-Leu-Ile-Pro-Ala-Glu-Gln-Gln-Met was used to design a pool of three synthetic oligonucleotides having the following sequences:

```
5' ATG TTC TGG AAC AGC CTG ATC CCC GCC GAG CAG CAG ATG 3'   [SEQ ID NO:7]
5' ATG TTC TGG AAC TCC CTG ATC CCC GCC GAG CAG CAG ATG 3'   [SEQ ID NO:8]
5' ATG TTC TGG AAC AGC TTG ATC CCC GCC GAG CAG CAG ATG 3'   [SEQ ID NO:9]
```

Figure 3F:
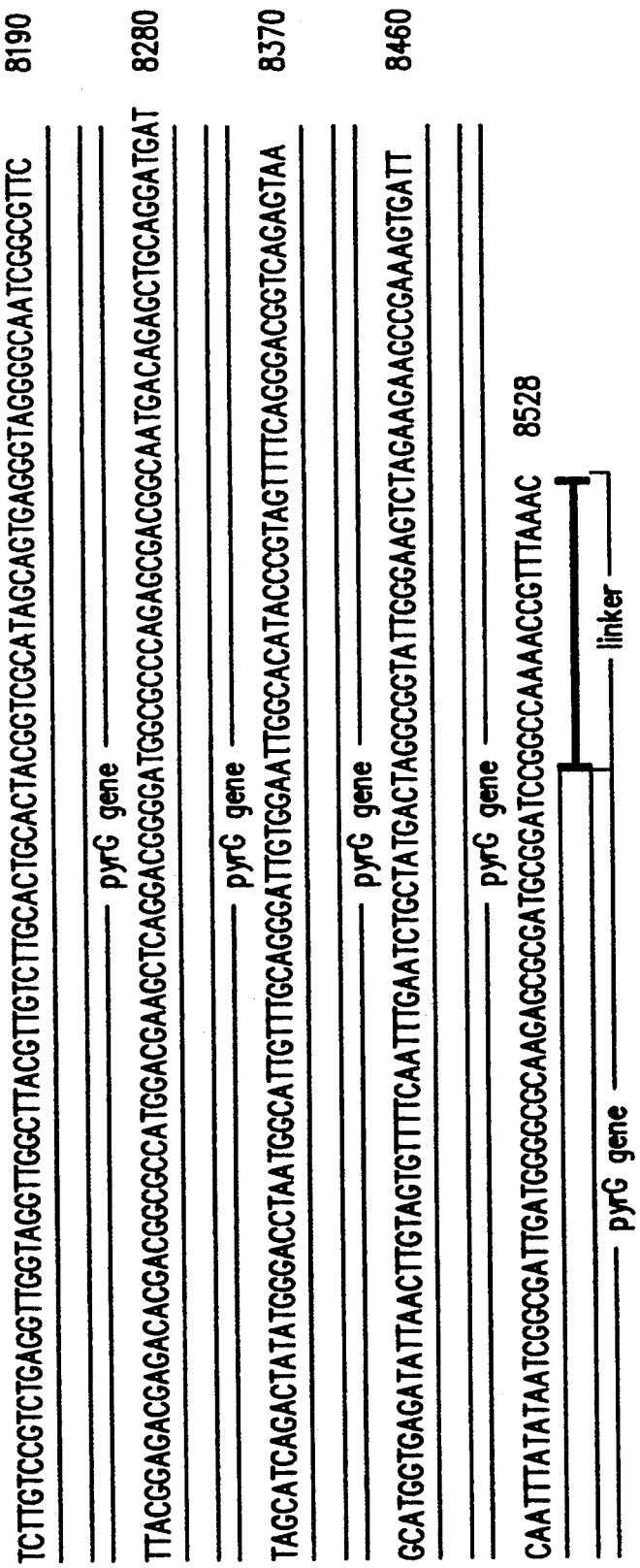

This peptide was chosen because the amino acids give minimally degenerate codon choices, i.e., the differences among the three synthetic oligonucleotides represent alternate codon choices where there was not strong bias in the known codon usage pattern for *A. niger*. This position of this proteolytic fragment corresponds to peptide 3 shown in FIG. 2 (amino acid nos. 487–499 of SEQ ID NOS:4 and 5). A clone containing a partial cDNA fragment was positively identified by hybridization with the synthetic DNA probe and nucleotide sequence analysis of this clone confirmed that it encoded catalase-R. This cloned cDNA segment was used to probe a library of *A. niger* genomic DNA. Subsequently, the entire catR gene, plus upstream and downstream transcriptional control elements, was assembled as a 9.0 kb HindIII-KhoI restriction fragment. The nucleotide sequence of the catR coding region has been determined and is given in FIG. 3 (SEQ ID NO:6).

2. Construction of a Catalase Expression Vector-Cassette (EC2) Used for Transformation of *A. niger*

Figure 1A:
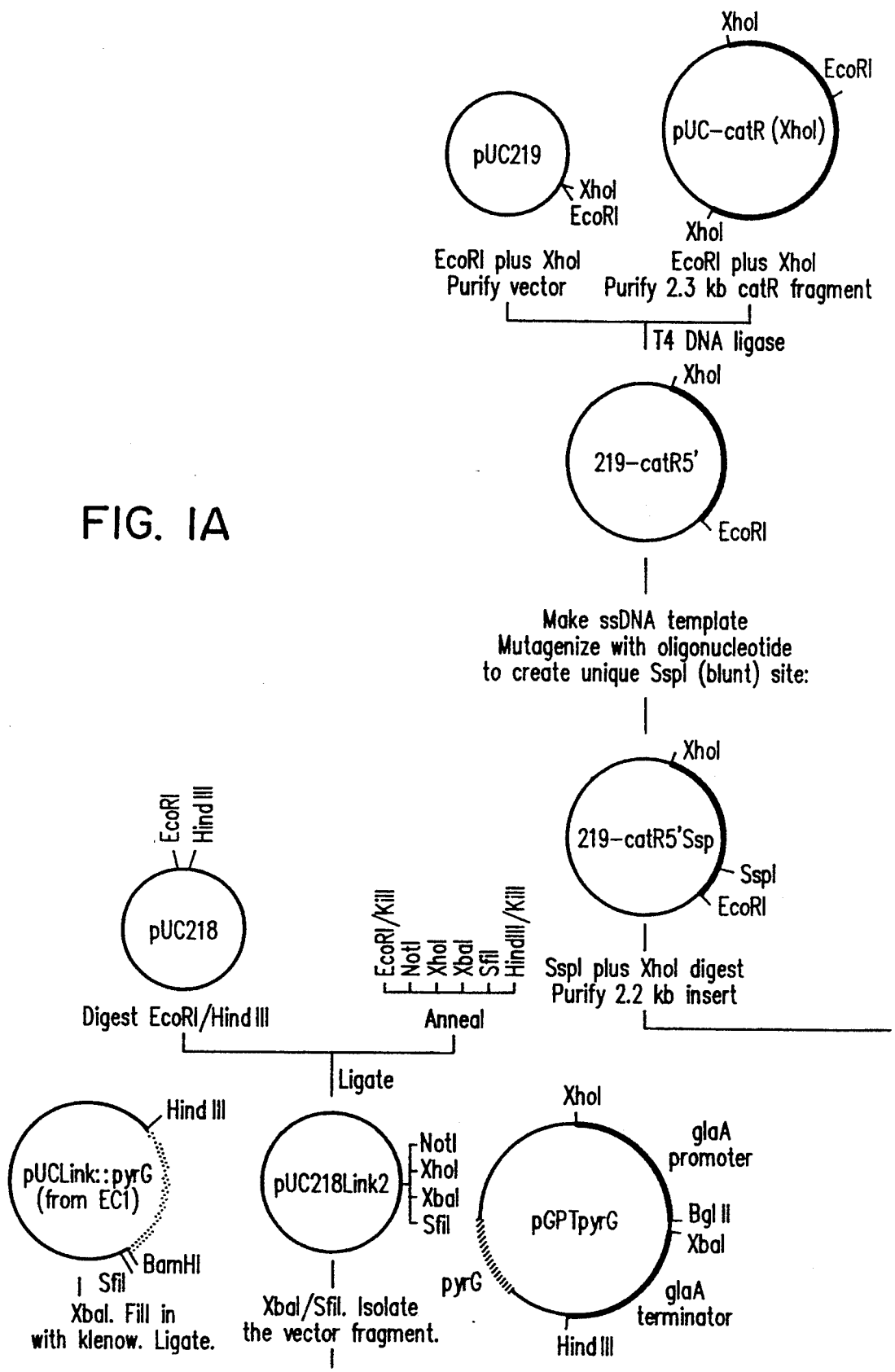
Figures 1, 1C:
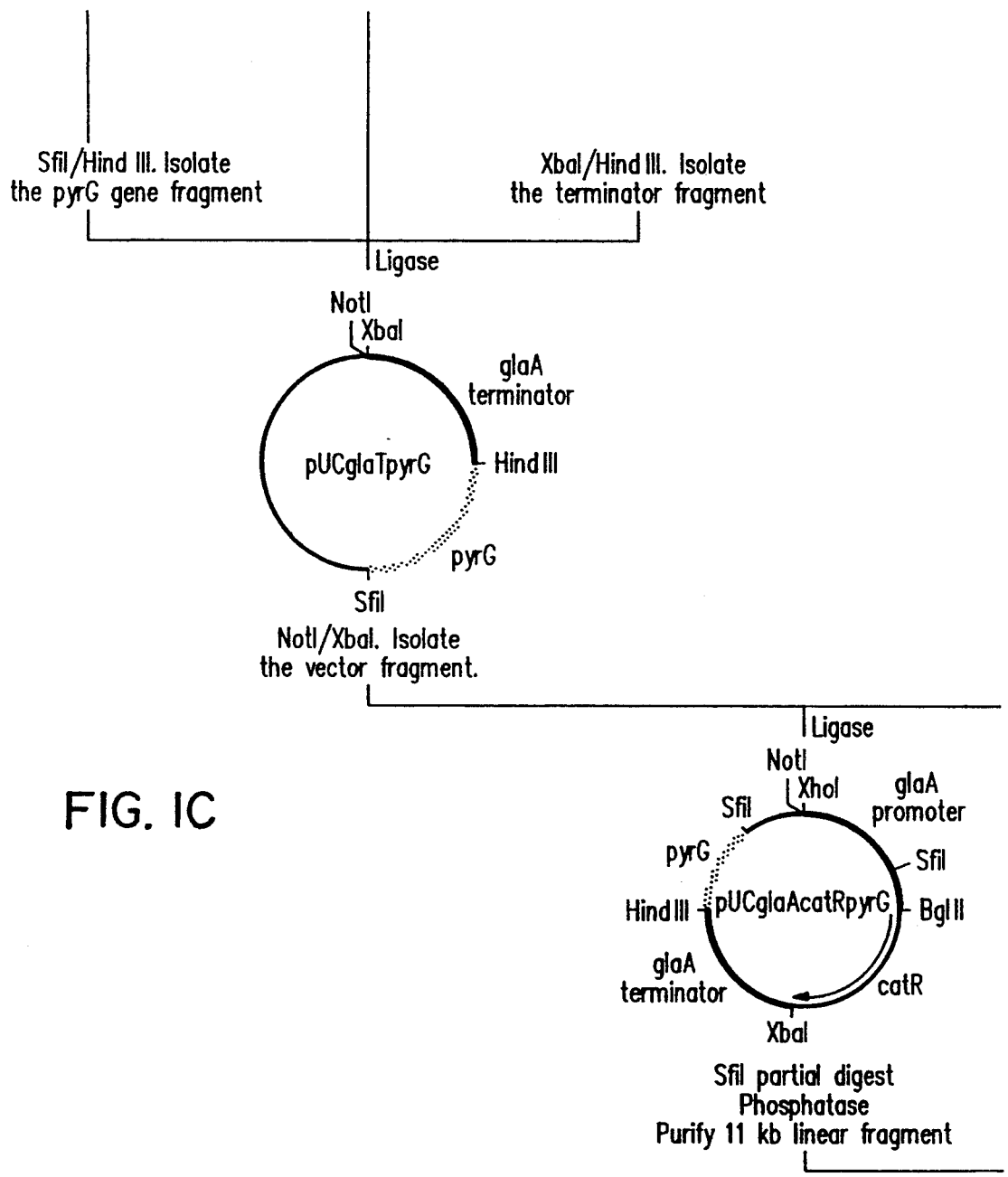

The catR expression vector used for these studies utilizes transcriptional and translational control signals from the well-characterized *A. niger* glucoamylase (glaA) gene. Unlike the catR promoter, the strong glaA promoter does not require $H_2O_2$ for induction. Instead, the glaA promoter responds to the presence of starch, maltose or other malto-oligosaccharides (Nunberg, et al., 1984 Mol. Cell. Biol. 4: 2306–2316; Barton, et al., 1972 J. Bacteriol. 111: 771–777; Fowler, et al., 1990 Curr. Genet. 18: 537–545). Thus, use of the glaA promoter allows construction of catalase production strains which are not dependent on the generation of hydrogen peroxide for induction of catalase synthesis. Construction of the vector-cassette for expression of catalase under transcriptional control of the glaA promoter is outlined in FIG. 1. The essential feature of this construct is that the glucoamylase-catalase expression unit (i.e., glaA promoter+catR coding region+glaA terminator) and the adjacent selectable marker (the *A. niger* pyrG gene) can be excised on a single NotI-PmeI restriction fragment (FIG. 1).

The catR coding region was joined to the glaA promoter utilizing a synthetic oligonucleotide linker (13 base pairs) designed to couple these two DNA segments via a BglII site in the glaA promoter to a unique SspI site four base pairs after the catR start codon (introduced by site-directed mutagenesis). Insertion of this linker restores the nucleotide sequence of catR to that which existed prior to the site-directed mutagenesis and precisely fuses the catR coding region to the glaA promoter. In a description of the glaA promoter region given by Fowler, et al., (1990 Curr. Genet. 18: 537–545) it was noted that there are DNA sequences far upstream of the start codon which are required for high level expression. These sequences, which presumably represent transcriptional enhancer elements, are included on the 1.9 kb glaA promoter segment included in construction of the catR expression cassette. Similarly, the glaA terminator region was linked to the 3'-end of catR via a naturally-occurring ClaI site downstream of the catalase-R gene stop codon. An XbaI site adjacent to ClaI was incorporated using a synthetic DNA linker and was then used to complete the terminator fusion. This terminator segment, which encodes information necessary for proper polyadenylation and termination of transcription, is the same segment as that which was used for Genencor's chymosin expression vector (Cullen, et al., 1987 Bio/Technol. 5: 369–376). A restriction fragment containing the *A. niger* pyrG gene (Wilson, et al., 1988 Nucl. Acids Res. 16: 2339) was subcloned adjacent to the glaA terminator such that the entire glucoamylase-catalase-selectable marker cassette was encoded on a single restriction fragment (the nucleotide sequence of this fragment (EC2L) is given in FIG. 3 (SEQ ID NO:6)).

3. Development of *A. niger* Strains to be Used in the Production of Catalase Features of the *A. niger* strain used as a host for expression of the glucoamylase-catalase cassette include a) uridine-requiring auxotrophy, specifically a pyrG auxotrophic mutation, b) deletion of the gene encoding glucose oxidase, goxA, and (c) a methionine-requiring auxotrophy, specifically mutation which renders the cells deficient in cystathionase (metC) activity. While the metC marker is not required for high level expression of catalase-R, it was included as a feature of the host strain to satisfy limited survivability regulation of government regulatory agencies. The catalase expression cassette described above was used to transform the *A. niger* ΔgoxA pyrG metC strain and the resulting transformants were screened in shake flask cultures for their ability to produce high levels of catalase. From these transformants, the highest catalase producers were selected for further study. Shake flask cultures were grown for two days at 33° C. in 50 ml of a liquid medium that was made according to the following recipe: For each liter of medium add maltodextrin [Staley 200, A. E. Staley Co., (100 g)], ammonium sulfate (4 g), calcium chloride (0.4 g), magnesium sulfate (0.6 g), corn steep liquor [Archer Daniels Midland Co., (10 g)], and potassium phosphate (3 g); The volume is brought to 500 ml with distilled water, the pH is adjusted to 7.0, and the solution is autoclaved; Separately a 500 ml solution of 12% calcium carbonate is made in distilled water, the pH is adjusted to 7.0, and the solution autoclaved. The two sterile mixtures were combined aseptically to give one liter of catalase production medium. After two days growth, the mycelia were harvested by filtration (Miracloth, Calbiochem, Inc.), and the cells were rapidly frozen in liquid nitrogen. The cells were disrupted by grinding the frozen pellet in an electric coffee grinder for approximately 60 sec or until a fine powder was obtained. The disrupted cells were resuspended in an extraction buffer that contained 100 mM sodium formate, pH 7, 0.01% sodium dodecylsulfate, and 1 mM each of phenylmethyl sulfonyl fluoride and pepstatin. Insoluble debris was removed by centrifugation at approximately 1500 ×g, and the activity of soluble catalase in the extract was measured by previously described methods (Patti and Bonet-Maury 1953 Bull Soc. Biol. 35: 1177; Teranishi, et al., 1974 Agric. Biol. Chem. 38: 1213). Specific methods for generation of the catalase production organisms are outlined below. The parental strain for all studies described herein was *A. niger* FS-1 (NRRL3).

Isolation of *A. niger* FS-1 pyrG Strains

5-Fluoro-orotic acid (FOA), a toxic analog of orotic acid, has been used to select uridine-requiring auxotrophs in filamentous fungi and yeasts (VanHartingveldt, et al., 1987 Mol. Gen. Genet. 206: 71–75). Fungal strains deficient in orotidine-5'-monophosphate decarboxylase (pyrG gene product), are resistant to FOA and require exogenous uridine for growth. The *A. niger* pyrG gene was cloned (Wilson, et al., 1988 Nucl. Acids Res. 16: 2339) and used as a selectable marker for the transformation of pyrG mutant strains. An advantage of using FOA as a positive selection for pyrG auxotrophs is that spontaneous mutants can be selected without need for excessive mutagenesis and screening. The method of selecting *A. niger* FS-1 pyrG mutants is as follows: Spores of *A. niger* FS-1 were spread onto the surface of minimal medium plates containing 2 mg/ml uridine and 1.2 mg/ml FOA. Resistant colonies (FOA$^r$) were evident after 2-3 days growth at 37° C. Spores from six FOA$^r$ colonies were streaked onto fresh medium containing FOA, and isolated colonies were picked for further analysis. Three of the six FOA$^r$ strains were shown to require uridine for growth. To determine which of the uridine-requiring strains had a non-functional pyrG gene, each of the strains was tested for its ability to be transformed (i.e., complemented) with a plasmid containing the *A. nidulans* pyrG gene. Only one strain, FS-1 pyrG1, gave transformants (an approximate frequency of 10 transformants per µg DNA) indicating that it carried a pyrG mutation. This strain was used for all subsequent experimentation.

Generation of *A. niger* FS-1 ΔgoxA Strains

Figure 4A:
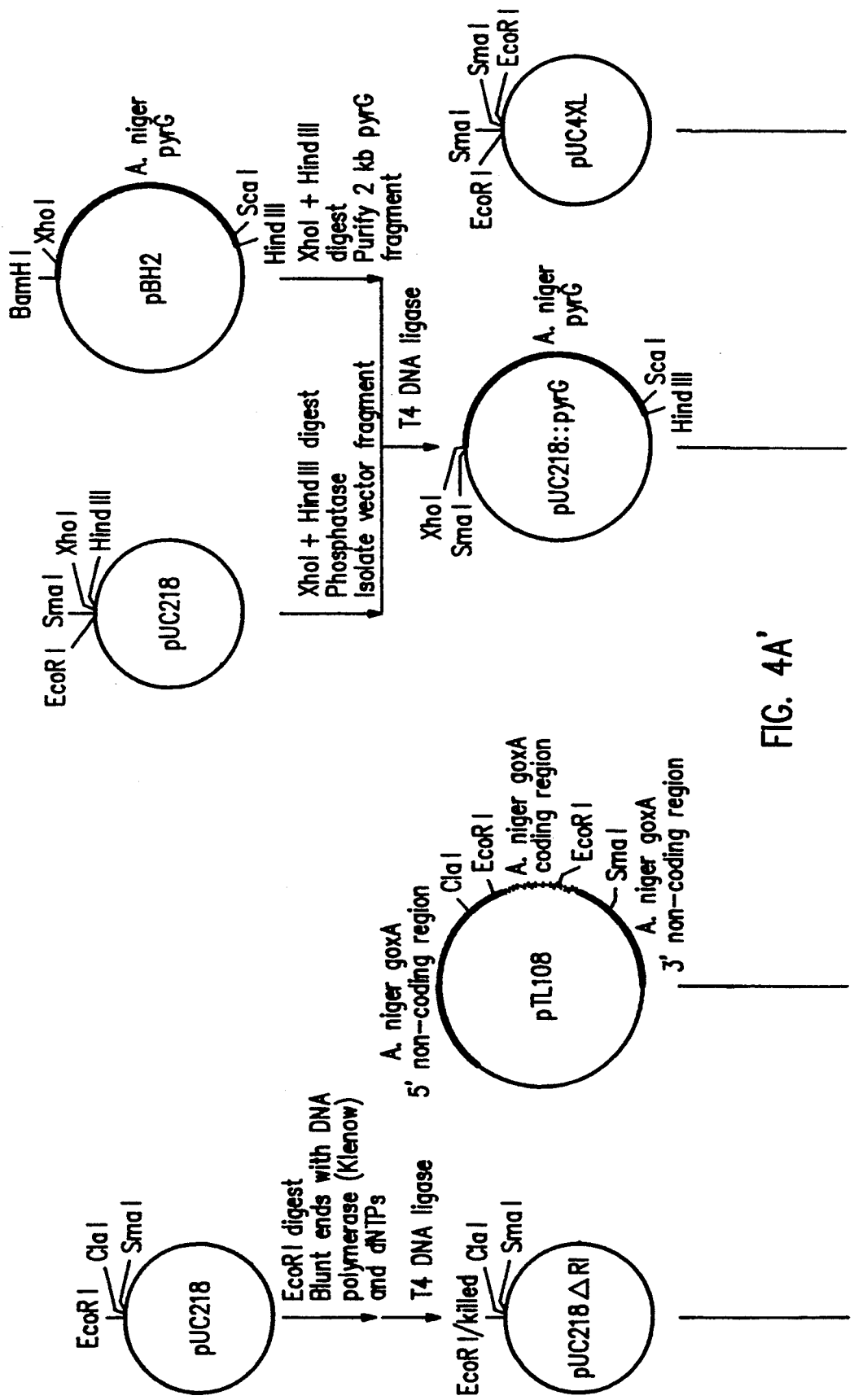
Figure 4B:
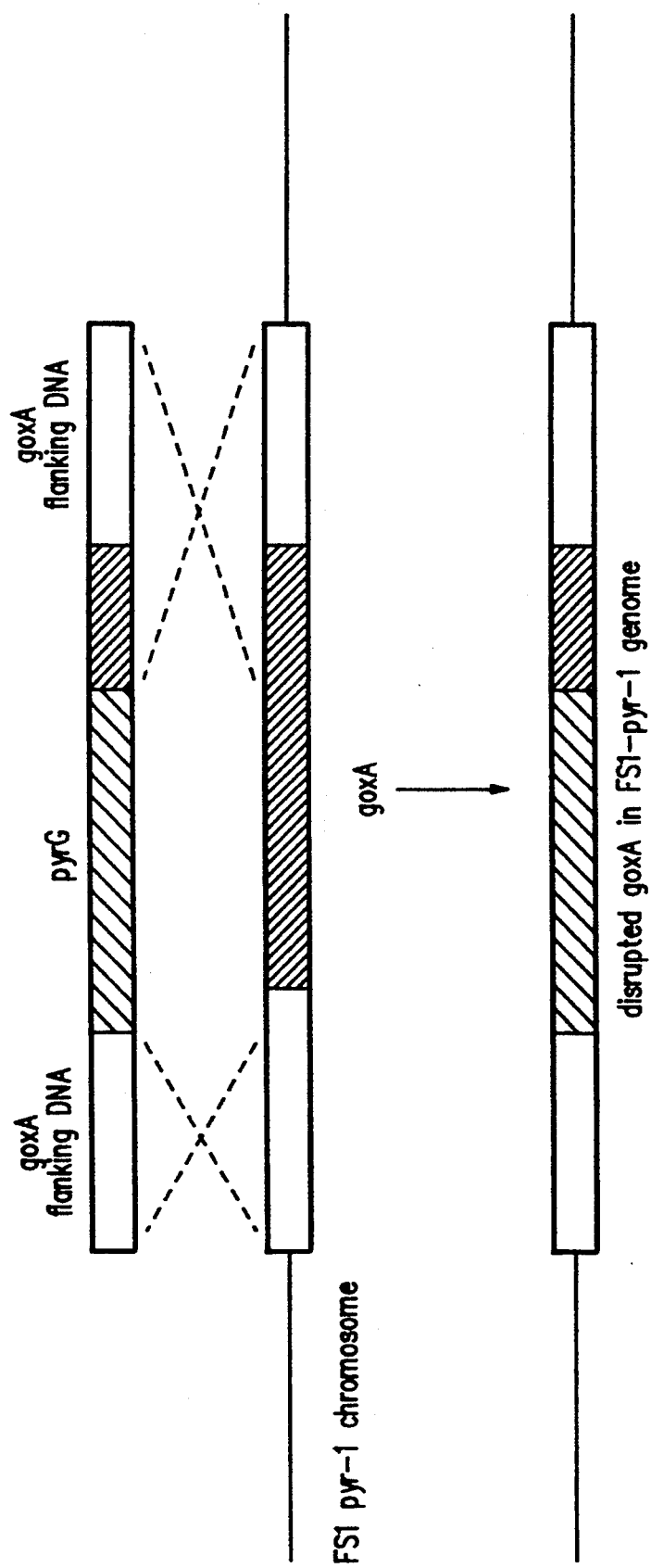

To generate a chromosomal deletion in the goxA gene, a vector was constructed which contained 5'- and 3'-flanking DNA sequences from the goxA gene and a selectable pyrG gene inserted in place of a portion of the goxA coding region (see FIG. 4). For complete information regarding the nucleotide sequence of the goxA gene, consult Frederick, et al., 1990 J. Biol. Chem. 265: 3793-3802 989 and Kriechbaum, et al., 1989 FEBS Lett. 255: 63-66. Briefly, a 4.1 kb ClaI-SmaI fragment comprising the *A. niger* FS-1 goxA gene was subcloned into a pUC218-derivative (from which the EcoRI site had previously been removed) to give pUC218goxA. The *A. niger* pyrG gene was isolated from pUC4XL as an EcoRI fragment having 27 bp and 16 bp of pUC4XL polylinker DNA at either end. The goxA coding region was subsequently removed by digestion with EcoRI and the remaining plasmid fragment was ligated with the EcoRI fragment containing the *A. niger* pyrG gene to create pUC218ΔgoxA. From this plasmid a 4.75 kb SmaI-XbaI restriction fragment which contains 5'- and 3'-flanking regions of the goxA gene with part of the goxA coding sequence removed and replaced with a functional pyrG gene was isolated. Use of this fragment to transform *A. niger* FS-1 pyrG1 with selection for uridine prototrophy resulted in the isolation of several strains which failed to give a blue color on glucose oxidase indicator plates (Witteveen, et al., 1990 Appl. Microbiol. Biotechnol. 33: 683-686). Southern blotting analysis of genomic DNA extracted from these goxA-deficient transformants indicated that the ΔgoxA::pyrG cassette had integrated via a homologous recombination event at the goxA locus (as diagramed in FIG. 4B). In other words, the selectable pyrG gene had replaced the goxA coding region.

Figure 5:
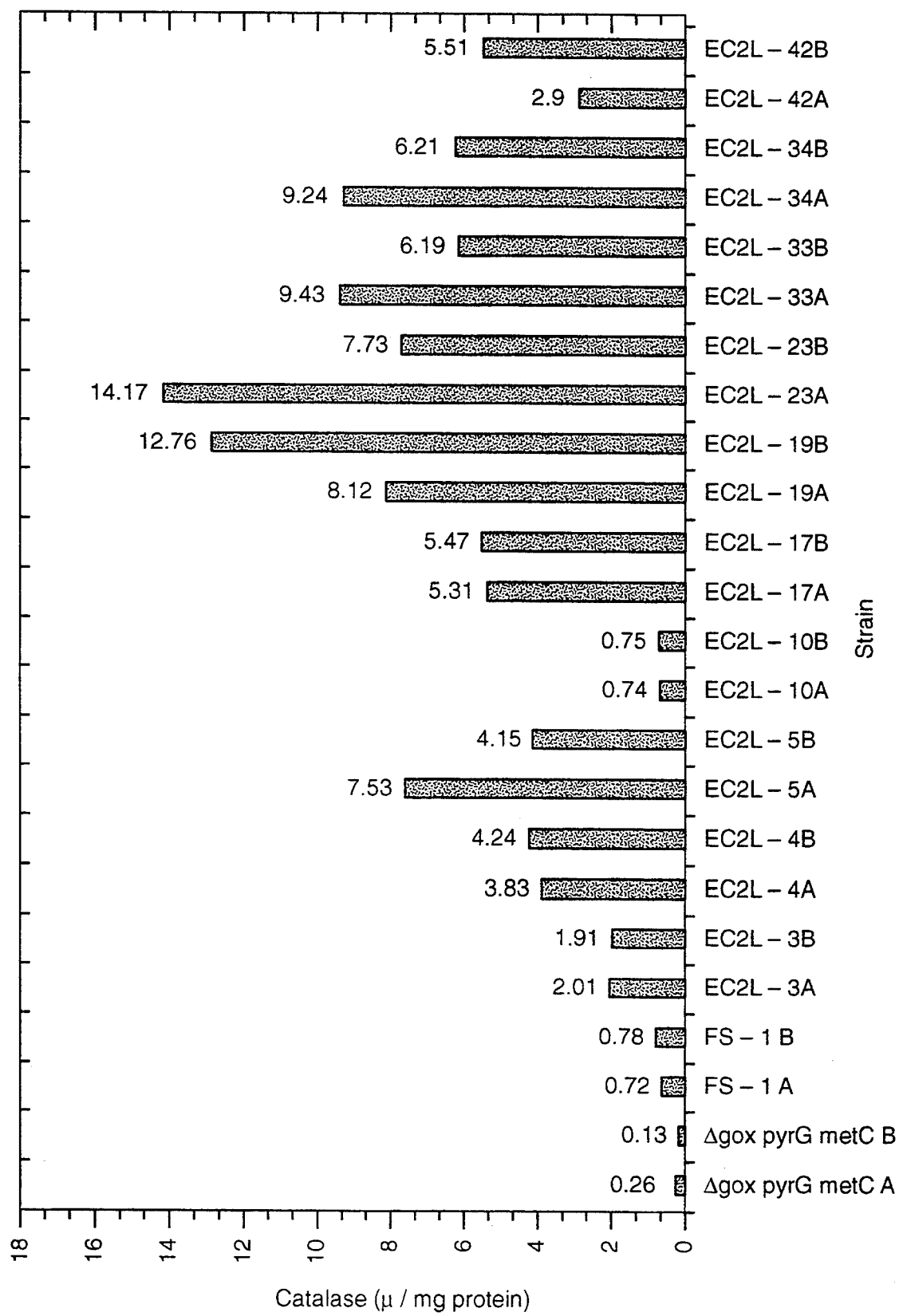

As shown in FIG. 5, catalase production in ΔgoxA mutants was approximately three- to six-fold lower than the parental strain FS-1. We interpret these data to indicate that in the absence of glucose oxidase little hydrogen peroxide is generated, and this in turn has an adverse effect on catalase induction.

Isolation of *A. niger* FS-1 ΔgoxA pyrG Strains

Spontaneous uridine-requiring mutants of *A. niger* FS-1 ΔgoxA were selected using FOA as described above. This step was necessary for subsequent transformation of the strain with the pyrG-based EC2 cassette.

Isolation of an *A. niger* FS-1 ΔgoxA pyrG metC Strain

In order to limit the survivability of a recombinant catalase production organism in the environment, a methionine-requiring auxotrophy was introduced in the following manner. Spores of *A. niger* FS-1 ΔgoxA pyrG were mutagenized with UV light (95% killing) and survivors were subjected to filtration enrichment in Aspergillus minimal medium. With this technique, unwanted prototrophs germinate and grow to form mycelia which can be removed by filtration. Auxotrophic cells cannot generate or grow in minimal medium, and therefore pass through porous filters (e.g., Miracloth, Calbiochem, Inc.). After several rounds of filtration and growth, the remaining spores were plated onto complete medium. Colonies were patched from these plates onto minimal medium agar and to fresh complete medium plates. Those which grew on complete medium but not on minimal agar were auxotrophic. From the population of auxotrophs, one colony was identified which grew on minimal medium supplemented with methionine. Upon further testing, it was discovered that the strain was defective in a specific step of the methionine biosynthetic pathway. Growth was supported by the addition of either homocysteine or methionine, but not by either homoserine or cystathionine. Based on the known biosynthetic pathway for methionine, it appears that this methionine-requiring auxotroph was deficient in cystathionase activity, and thus, it was given the designation of metC by convention with other organisms.

Transformation of the *A. niger* FS-1 ΔgoxA pyrG metC Strain and Characterization of Catalase Overproducing Strains The catalase expression cassette (in linear form) was isolated following digestion of the pUC-EC2 plasmid with PmeI and NotI and purification of the EC2 fragment by preparative gel electrophoresis. The purified DNA fragment was then used to transform the *A. niger* ΔgoxA pyrG metC strain, and prototrophic transformants were screened in shake flask culture for their ability to produce catalase. From approximately fifty transformants screened in shake flasks, ten were identified that produced significantly higher catalase levels than control strains. These ten strains were re-evaluated in duplicate shake flask cultures, and the results of catalase activity assays are shown in FIG. 5. Nine of the ten strains produced significantly higher levels of catalase-R than the parent strain FS-1. Two of the transformants (EC2L-19, EC2L-23) produced catalase yields in shake flask cultures that were roughly ten to fifteen times the level produced by *A. niger* FS-1, and these strains were chosen for testing under large scale production conditions. Fermentation experiments at the 10 liter and 50,000 liter scale have shown that catalase-R production from transformant EC2L-23 correspond to the level of catalase-R expression seen in shake flask studies.

Furthermore, HPLC analyses of organic acids produced during fermentation of *A. niger* EC2L-23 and the parental strain FS-1 gave the following yields of sodium gluconate:

| Strain | sodium gluconate (mg/L) |
| --- | --- |
| FS-1 | >200,000 |
| EC2L-23 (run 27) | 48 |
| EC2L-23 (run 28) | 123 |

These data show a dramatic decrease in the production of sodium gluconate waste material by transformant EC2L-23.

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 29 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:1:

```
GATCAGATCT GGATCCATCG ATAGTCTAG                                       29
```

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:2:

```
GATCTCAGCA ATGCGTC                                                    17
```

( 2 ) INFORMATION FOR SEQ ID NO:3:

( i ) SEQUENCE CHARACTERISTICS:
        ( A ) LENGTH: 36 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:3:

```
AAAACCGTTT AAACGGCGCG CCTTAATTAA GGAAAA                               36
```

( 2 ) INFORMATION FOR SEQ ID NO:4:

( i ) SEQUENCE CHARACTERISTICS:
        ( A ) LENGTH: 3107 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: join(327..620, 683..907, 969..1385, 1440..1604,
            1654..2745)

( x i ) SEQUENCE DESCRIPTION: SEQ ID NO:4:

```
CTTGTCACCG AGTGCCCGTT TGTCACTTGT TGTGGTGATC TTGAGCACAT CGCGTTCCTC      60

TCGTCTCATC ACATCGAGTG ATCAACATTG CATGACCCTA GTGGAGCCCC TTCGTCTCCC     120

AACAGGAGGG TCCGGATTAC CAAGTCCCGA CACCGTTTGG CTGTAATTCG ACTCAAATTC     180

TGGATTCGTA GCTTAACTAA GACGCGTGGT CTGTTAACCG GCCTCGCCAT GGATGCCGAT     240

ATAAGGACCC TAGGGGACTC CCCCCTGGTG ACTCTCGTCG AAGATCGCA GCACTCTGAA      300

TTCTCCTAGT CTTCGTTTAC TCCGCC ATG CGT CAT TTC TGG CTT TTG CCA GCT     353
                             Met Arg His Phe Trp Leu Leu Pro Ala
                              1               5

GTT GCT GGT ATC GCT GGG GCT CAA TGC CCC TAC CTG TCG GGT GAA ATG      401
```

|   |   |   |   |   |   |   |   |   |   |   |   |   |   |   |   |   |
|---|---|---|---|---|---|---|---|---|---|---|---|---|---|---|---|---|
| Val | Ala | Gly | Ile | Ala | Gly | Ala | Gln | Cys | Pro | Tyr | Leu | Ser | Gly | Glu | Met | |
| 10 | | | | 15 | | | | | 20 | | | | | | 25 | |

| AGT | TTC | ACC | CAG | GAG | CAG | GAC | AAT | GCT | GGC | GAT | ACC | ATT | GAG | GTC | ACG | 449 |
|-----|-----|-----|-----|-----|-----|-----|-----|-----|-----|-----|-----|-----|-----|-----|-----|-----|
| Ser | Phe | Thr | Gln | Glu | Gln | Asp | Asn | Ala | Gly | Asp | Thr | Ile | Glu | Val | Thr | |
|     |     |     |     | 30  |     |     |     |     | 35  |     |     |     |     | 40  |     |     |

| GAG | CAG | CCC | ATT | GAC | AAC | ACC | CTG | TAT | GTC | AAT | GAC | ACC | GGT | AGC | TAC | 497 |
| Glu | Gln | Pro | Ile | Asp | Asn | Thr | Leu | Tyr | Val | Asn | Asp | Thr | Gly | Ser | Tyr | |
|     |     |     | 45  |     |     |     |     | 50  |     |     |     |     | 55  |     |     |     |

| ATG | ACT | ACC | GAC | TTT | GGC | ACT | CCG | ATC | TCC | GAC | CAG | ACC | AGT | CTC | AAG | 545 |
| Met | Thr | Thr | Asp | Phe | Gly | Thr | Pro | Ile | Ser | Asp | Gln | Thr | Ser | Leu | Lys | |
|     |     | 60  |     |     |     |     | 65  |     |     |     |     | 70  |     |     |     |     |

| GCC | GGG | CCC | CGT | GGT | CCT | ACC | CTG | TTG | GAG | GAC | TTT | ATC | TTC | CGT | CAG | 593 |
| Ala | Gly | Pro | Arg | Gly | Pro | Thr | Leu | Leu | Glu | Asp | Phe | Ile | Phe | Arg | Gln | |
|     | 75  |     |     |     |     | 80  |     |     |     |     | 85  |     |     |     |     |     |

| AAG | CTT | CAG | CGG | TTC | GAC | CAT | GAG | CGT | | | | | | | | 640 |
| Lys | Leu | Gln | Arg | Phe | Asp | His | Glu | Arg | GTAAGTACAG TAACTGCTGC | | | | | | | |
| 90  |     |     |     |     |     | 95  |     |     | | | | | | | | |

GGTGTGTAGT AACAATAAAT TGACCCAGTG GTTTTCAATT AG GTC CCC GAG CGC   694
                                             Val Pro Glu Arg
                                             100

| GTC | GTC | CAC | GCC | CGT | GGT | GCC | GGT | GCA | TAT | GGT | ACT | TTC | AAA | TCC | TAC | 742 |
| Val | Val | His | Ala | Arg | Gly | Ala | Gly | Ala | Tyr | Gly | Thr | Phe | Lys | Ser | Tyr | |
|     |     | 105 |     |     |     |     | 110 |     |     |     |     | 115 |     |     |     |     |

| GCC | GAC | TGG | TCG | AAC | GTC | ACG | GCT | GCC | GAT | TTC | TTG | AGT | GCC | AAC | GAT | 790 |
| Ala | Asp | Trp | Ser | Asn | Val | Thr | Ala | Ala | Asp | Phe | Leu | Ser | Ala | Asn | Asp | |
|     | 120 |     |     |     |     | 125 |     |     |     |     | 130 |     |     |     |     |     |

| AAG | GAG | ACC | CCT | ATG | TTC | TGT | CGC | TTC | TCT | ACT | GTG | GTC | GGT | TTC | CGT | 838 |
| Lys | Glu | Thr | Pro | Met | Phe | Cys | Arg | Phe | Ser | Thr | Val | Val | Gly | Phe | Arg | |
| 135 |     |     |     |     | 140 |     |     |     |     | 145 |     |     |     |     | 150 |     |

| GGT | AGT | GTT | GAC | ACT | GCG | CGT | GAT | GTT | CAC | GGT | CAC | GCT | TGT | CGG | TTC | 886 |
| Gly | Ser | Val | Asp | Thr | Ala | Arg | Asp | Val | His | Gly | His | Ala | Cys | Arg | Phe | |
|     |     |     |     | 155 |     |     |     |     | 160 |     |     |     |     | 165 |     |     |

| TAC | ACT | GAC | GAG | GGT | AAC | TAT | | | | | | | | | | 937 |
| Tyr | Thr | Asp | Glu | Gly | Asn | Tyr | GGTATCTTGA TATGGTCACC CAACAATAAT | | | | | | | | |
|     |     | 170 |     |     |     |     | | | | | | | | | | |

TCAATACATG CTAACAGATA TGTCTCTACT A GAC ATC GTC GGT ATC AAT TTC   989
                                  Asp Ile Val Gly Ile Asn Phe
                                      175              180

| GCC | CCC | TTC | TTC | ATC | CAG | GAC | GCC | ATC | CAG | TTC | CCC | GAT | CTT | GTC | CAC | 1037 |
| Ala | Pro | Phe | Phe | Ile | Gln | Asp | Ala | Ile | Gln | Phe | Pro | Asp | Leu | Val | His | |
|     |     |     |     | 185 |     |     |     |     | 190 |     |     |     |     | 195 |     |      |

| GCC | ATC | AAG | CCC | ATG | CCC | AAC | AAT | GAG | ATC | CCC | CAG | GCC | GCT | ACT | GCA | 1085 |
| Ala | Ile | Lys | Pro | Met | Pro | Asn | Asn | Glu | Ile | Pro | Gln | Ala | Ala | Thr | Ala | |
|     |     |     | 200 |     |     |     |     | 205 |     |     |     |     | 210 |     |     |      |

| CAC | ACT | TCC | GCT | TGG | GAC | TTC | TTC | AGC | CAG | CAG | AGC | ACT | GCC | CTC | CAC | 1133 |
| His | Thr | Ser | Ala | Trp | Asp | Phe | Phe | Ser | Gln | Gln | Ser | Thr | Ala | Leu | His | |
|     |     |     | 215 |     |     |     |     | 220 |     |     |     |     | 225 |     |     |      |

| AGT | GCC | TTG | TGG | CTG | ATG | TCT | GGT | AAC | GGT | ATT | CCT | CGT | TCT | TTC | CGC | 1181 |
| Ser | Ala | Leu | Trp | Leu | Met | Ser | Gly | Asn | Gly | Ile | Pro | Arg | Ser | Phe | Arg | |
|     |     | 230 |     |     |     |     | 235 |     |     |     |     | 240 |     |     |     |      |

| CAC | ATG | AAC | GGC | TAC | GGA | GTC | CAC | AGC | TTC | CGC | TTC | GTC | GCT | GCC | AAT | 1229 |
| His | Met | Asn | Gly | Tyr | Gly | Val | His | Ser | Phe | Arg | Phe | Val | Ala | Ala | Asn | |
| 245 |     |     |     |     | 250 |     |     |     |     | 255 |     |     |     |     | 260 |      |

| GGC | ACT | TCC | AAG | GTG | GTG | CGA | ACA | CCT | TGG | AAG | TCC | CAA | CAG | GGT | GTT | 1277 |
| Gly | Thr | Ser | Lys | Val | Val | Arg | Thr | Pro | Trp | Lys | Ser | Gln | Gln | Gly | Val | |
|     |     |     |     | 265 |     |     |     |     | 270 |     |     |     |     | 275 |     |      |

| GCC | AGT | CTG | GTG | TGG | GAT | GAA | GCT | CAG | GCC | GCT | GCT | GGT | AAG | AAC | AGT | 1325 |
| Ala | Ser | Leu | Val | Trp | Asp | Glu | Ala | Gln | Ala | Ala | Ala | Gly | Lys | Asn | Ser | |
|     |     |     | 280 |     |     |     |     | 285 |     |     |     |     | 290 |     |     |      |

| GAC | TAC | CAC | CGC | CAG | GAT | CTG | TAC | AAT | GCG | ATG | CCC | AAT | GGC | CAC | TAC | 1373 |

```
Asp Tyr His Arg Gln Asp Leu Tyr Asn Ala Met Pro Asn Gly His Tyr
        295                 300                 305

CCG AAA TAC GAG GTCAGCCAAT CCCTTGATGT CTATCGATAG AGCCTTTTGC              1425
Pro Lys Tyr Glu
        310

TGACAATCCC CTAG CTC CAA GCC CAG ATC ATG GAT GAG GCT GAC ATG CTT          1475
                Leu Gln Ala Gln Ile Met Asp Glu Ala Asp Met Leu
                            315                 320

CGT TTC GGC TTC GAC CTT CTG GAT CCC ACC AAG TTG GTC CCC GAG GAG          1523
Arg Phe Gly Phe Asp Leu Leu Asp Pro Thr Lys Leu Val Pro Glu Glu
325                 330                 335                 340

GTT GTC CCT TAC ACT CCT CTC GGA ATG ATG GAG CTC AAT GCC AAC CCC          1571
Val Val Pro Tyr Thr Pro Leu Gly Met Met Glu Leu Asn Ala Asn Pro
                345                 350                 355

ACC AAC TAC TTT GCT GAA GTT GAA CAG GCT GGT GTATGTATTC CCCATTCATC        1624
Thr Asn Tyr Phe Ala Glu Val Glu Gln Ala Gly
                360                 365

AAATGCCAGA CATAATCTAA CTTCTGCAG TTC CAA CCC GGT CAC GTC GTT CCT          1677
                               Phe Gln Pro Gly His Val Val Pro
                                       370                 375

GGC ATT GAC TTC ACC GAC GAC CCC CTG CTG CAA GGC CGT CTC TTC TCC          1725
Gly Ile Asp Phe Thr Asp Asp Pro Leu Leu Gln Gly Arg Leu Phe Ser
                380                 385                 390

TAC CTC GAC ACT CAG TTG ACC CGT CAC GGC GGT CCC AAC TTC GAG CAA          1773
Tyr Leu Asp Thr Gln Leu Thr Arg His Gly Gly Pro Asn Phe Glu Gln
                395                 400                 405

ATC CCC GTC AAC CGT CCT CGC AAG CCC GTT CAC AAC AAC AAC CGT GAC          1821
Ile Pro Val Asn Arg Pro Arg Lys Pro Val His Asn Asn Asn Arg Asp
                410                 415                 420

GGC TTC GGC CAG CAG CAG ATC CCC ACC AAC AAC TGG GCC TAC ACC CCC          1869
Gly Phe Gly Gln Gln Gln Ile Pro Thr Asn Asn Trp Ala Tyr Thr Pro
425                 430                 435

AAC AGC ATG AGC AAC GGT TAC CCC ATG CAA GCC AAC CAG ACC CAG GGT          1917
Asn Ser Met Ser Asn Gly Tyr Pro Met Gln Ala Asn Gln Thr Gln Gly
440                 445                 450                 455

CAT GGT TTC TTC ACC GCG CCC TAC CGC TAC GCT TCC GGC CAT CTC GTC          1965
His Gly Phe Phe Thr Ala Pro Tyr Arg Tyr Ala Ser Gly His Leu Val
                460                 465                 470

CGC CAG ACC AGC CCG ACC TTC AAT GAC CAC TGG TCC CAG CCC GCC ATG          2013
Arg Gln Thr Ser Pro Thr Phe Asn Asp His Trp Ser Gln Pro Ala Met
                475                 480                 485

TTC TGG AAC TCT CTG ATC CCC GCT GAG CAG CAG ATG GTT GTC AAC GCC          2061
Phe Trp Asn Ser Leu Ile Pro Ala Glu Gln Gln Met Val Val Asn Ala
                490                 495                 500

ATT GTC TTT GAG AAC TCC AAG GTT AAC AGC CCC CAC GTT CGG AAG AAC          2109
Ile Val Phe Glu Asn Ser Lys Val Asn Ser Pro His Val Arg Lys Asn
        505                 510                 515

GTT GTC AAC CAG CTG AAC ATG GTC AAC AAC AAC CTC GCC GTC CGT GTC          2157
Val Val Asn Gln Leu Asn Met Val Asn Asn Asn Leu Ala Val Arg Val
520                 525                 530                 535

GCT CGT GGT CTT GGT CTC GAT GAG CCC TCC CCC AAC CCG ACT TAC TAC          2205
Ala Arg Gly Leu Gly Leu Asp Glu Pro Ser Pro Asn Pro Thr Tyr Tyr
                540                 545                 550

ACC TCC AAC AAG ACC TCC AAC GTC GGT ACC TTC GGC AAG CCC CTC CTC          2253
Thr Ser Asn Lys Thr Ser Asn Val Gly Thr Phe Gly Lys Pro Leu Leu
                555                 560                 565

AGC ATC GAG GGT CTG CAG GTC GGC TTC CTG GCC TCG AAC TCC CAC CCC          2301
Ser Ile Glu Gly Leu Gln Val Gly Phe Leu Ala Ser Asn Ser His Pro
                570                 575                 580

GAA TCC ATC AAG CAG GGC CAG GCC ATG GCC GCG CAG TTC TCT GCC GCT          2349
```

|         |     |     |     |     |     |     |     |     |     |     |     |     |     |     |     |      |
| ------- | --- | --- | --- | --- | --- | --- | --- | --- | --- | --- | --- | --- | --- | --- | --- | ---- |
| Glu     | Ser | Ile | Lys | Gln | Gly | Gln | Ala | Met | Ala | Ala | Gln | Phe | Ser | Ala | Ala |      |
|         | 585 |     |     |     | 590 |     |     |     |     | 595 |     |     |     |     |     |      |
| GGC     | GTC | GAC | CTG | AAC | ATT | GTC | ACC | GAG | GCC | TAC | GCC | GAT | GGT | GTC | AAC | 2397 |
| Gly     | Val | Asp | Leu | Asn | Ile | Val | Thr | Glu | Ala | Tyr | Ala | Asp | Gly | Val | Asn |      |
| 600     |     |     |     |     | 605 |     |     |     |     | 610 |     |     |     |     | 615 |      |
| ACC     | ACC | TAC | GCC | CTG | TCT | GAT | GCC | ATC | GAC | TTT | GAC | GCC | CTC | ATC | ATC | 2445 |
| Thr     | Thr | Tyr | Ala | Leu | Ser | Asp | Ala | Ile | Asp | Phe | Asp | Ala | Leu | Ile | Ile |      |
|         |     |     |     | 620 |     |     |     |     | 625 |     |     |     |     | 630 |     |      |
| GCC     | GAT | GGT | GTG | CAG | AGC | CTC | TTC | GCC | TCC | CCC | GCT | CTC | GCT | AAC | CAG | 2493 |
| Ala     | Asp | Gly | Val | Gln | Ser | Leu | Phe | Ala | Ser | Pro | Ala | Leu | Ala | Asn | Gln |      |
|         |     |     | 635 |     |     |     |     | 640 |     |     |     |     | 645 |     |     |      |
| ATG     | AAC | TCT | ACC | GCC | ACC | TCT | ACT | CTC | TAC | CCT | CCT | GCC | AGA | CCT | TTC | 2541 |
| Met     | Asn | Ser | Thr | Ala | Thr | Ser | Thr | Leu | Tyr | Pro | Pro | Ala | Arg | Pro | Phe |      |
|         |     | 650 |     |     |     |     | 655 |     |     |     |     | 660 |     |     |     |      |
| CAG     | ATC | CTG | GTC | GAT | TCT | TTC | AGG | TAC | GGT | AAG | CCC | GTG | GCT | GCT | GTC | 2589 |
| Gln     | Ile | Leu | Val | Asp | Ser | Phe | Arg | Tyr | Gly | Lys | Pro | Val | Ala | Ala | Val |      |
|         | 665 |     |     |     |     | 670 |     |     |     |     | 675 |     |     |     |     |      |
| GGC     | AGT | GGC | AGT | GTT | GCG | CTC | AAG | AAC | GCT | GGT | ATT | GAT | TCC | TCC | CGC | 2637 |
| Gly     | Ser | Gly | Ser | Val | Ala | Leu | Lys | Asn | Ala | Gly | Ile | Asp | Ser | Ser | Arg |      |
| 680     |     |     |     |     | 685 |     |     |     |     | 690 |     |     |     |     | 695 |      |
| TCT     | GGT | GTG | TAC | ACT | GGC | TCG | AGC | GAG | ACG | ACG | GAG | AAG | ATC | GCC | AAG | 2685 |
| Ser     | Gly | Val | Tyr | Thr | Gly | Ser | Ser | Glu | Thr | Thr | Glu | Lys | Ile | Ala | Lys |      |
|         |     |     |     | 700 |     |     |     |     | 705 |     |     |     |     | 710 |     |      |
| GAG     | GTC | TTG | GAG | GGA | CTC | TAC | ACT | TTC | CGT | TTT | GTG | GAC | CGG | TTT | GCG | 2733 |
| Glu     | Val | Leu | Glu | Gly | Leu | Tyr | Thr | Phe | Arg | Phe | Val | Asp | Arg | Phe | Ala |      |
|         |     |     | 715 |     |     |     |     | 720 |     |     |     |     | 725 |     |     |      |
| CTG     | GAT | GAG | TAAGGGTATC | ACGTTTGTAC | TTGTACTCAC | GTTCATCGTT |     |     |     |     |     |     |     |     |     | 2782 |
| Leu     | Asp | Glu |     |     |     |     |     |     |     |     |     |     |     |     |     |      |
|         |     | 730 |     |     |     |     |     |     |     |     |     |     |     |     |     |      |

| TGTGATGATA | CATTGATTGA | TCGATAGATA | TTTTGTGAGA | TAGATAGAGT | ATACTAGAGW | 2842 |
| GKACATATCT | CTACTGATGA | GGTGTTGTGC | TGCTGCAACA | CATATTTATG | AATATATATT | 2902 |
| CTCTTCTTTG | TGAAAGCTAG | CCTTCTATAT | AATCAGCAAT | GGTTAACTCT | TCCAATTCTA | 2962 |
| TAGATACCAA | TCACCTAACC | CACTCGGAAT | GACGACAGAA | AACATCGACA | TGTTCGCCCA | 3022 |
| AGTAAAGCTA | CTTGAACTTC | TACATTTATG | CTATGCTGGA | GTCCTCTCAT | AAGTCCAGAA | 3082 |
| TAAACAAAGA | GATCCGATCC | TGCTC      |            |            |            | 3107 |

( 2 ) INFORMATION FOR SEQ ID NO:5:

( i ) SEQUENCE CHARACTERISTICS:
        ( A ) LENGTH: 730 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| Met | Arg | His | Phe | Trp | Leu | Leu | Pro | Ala | Val | Ala | Gly | Ile | Ala | Gly | Ala |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Gln | Cys | Pro | Tyr | Leu | Ser | Gly | Glu | Met | Ser | Phe | Thr | Gln | Glu | Gln | Asp |
|     |     |     | 20  |     |     |     |     | 25  |     |     |     |     | 30  |     |     |
| Asn | Ala | Gly | Asp | Thr | Ile | Glu | Val | Thr | Glu | Gln | Pro | Ile | Asp | Asn | Thr |
|     |     | 35  |     |     |     |     | 40  |     |     |     |     | 45  |     |     |     |
| Leu | Tyr | Val | Asn | Asp | Thr | Gly | Ser | Tyr | Met | Thr | Thr | Asp | Phe | Gly | Thr |
|     | 50  |     |     |     |     | 55  |     |     |     |     | 60  |     |     |     |     |
| Pro | Ile | Ser | Asp | Gln | Thr | Ser | Leu | Lys | Ala | Gly | Pro | Arg | Gly | Pro | Thr |
| 65  |     |     |     |     | 70  |     |     |     |     | 75  |     |     |     |     | 80  |
| Leu | Leu | Glu | Asp | Phe | Ile | Phe | Arg | Gln | Lys | Leu | Gln | Arg | Phe | Asp | His |
|     |     |     |     | 85  |     |     |     |     | 90  |     |     |     |     | 95  |     |
| Glu | Arg | Val | Pro | Glu | Arg | Val | Val | His | Ala | Arg | Gly | Ala | Gly | Ala | Tyr |

|     |     |     | 100 |     |     |     |     | 105 |     |     |     |     | 110 |     |
| --- | --- | --- | --- | --- | --- | --- | --- | --- | --- | --- | --- | --- | --- | --- |
| Gly | Thr | Phe | Lys | Ser | Tyr | Ala | Asp | Trp | Ser | Asn | Val | Thr | Ala | Ala | Asp |
|     |     |     | 115 |     |     |     |     | 120 |     |     |     |     | 125 |     |     |
| Phe | Leu | Ser | Ala | Asn | Asp | Lys | Glu | Thr | Pro | Met | Phe | Cys | Arg | Phe | Ser |
|     |     |     | 130 |     |     |     | 135 |     |     |     | 140 |     |     |     |     |
| Thr | Val | Val | Gly | Phe | Arg | Gly | Ser | Val | Asp | Thr | Ala | Arg | Asp | Val | His |
| 145 |     |     |     |     | 150 |     |     |     |     | 155 |     |     |     |     | 160 |
| Gly | His | Ala | Cys | Arg | Phe | Tyr | Thr | Asp | Glu | Gly | Asn | Tyr | Asp | Ile | Val |
|     |     |     |     | 165 |     |     |     |     | 170 |     |     |     |     | 175 |     |
| Gly | Ile | Asn | Phe | Ala | Pro | Phe | Phe | Ile | Gln | Asp | Ala | Ile | Gln | Phe | Pro |
|     |     |     | 180 |     |     |     |     | 185 |     |     |     |     | 190 |     |     |
| Asp | Leu | Val | His | Ala | Ile | Lys | Pro | Met | Pro | Asn | Asn | Glu | Ile | Pro | Gln |
|     |     |     | 195 |     |     |     |     | 200 |     |     |     |     | 205 |     |     |
| Ala | Ala | Thr | Ala | His | Thr | Ser | Ala | Trp | Asp | Phe | Phe | Ser | Gln | Gln | Ser |
|     |     | 210 |     |     |     |     | 215 |     |     |     |     | 220 |     |     |     |
| Thr | Ala | Leu | His | Ser | Ala | Leu | Trp | Leu | Met | Ser | Gly | Asn | Gly | Ile | Pro |
| 225 |     |     |     |     | 230 |     |     |     |     | 235 |     |     |     |     | 240 |
| Arg | Ser | Phe | Arg | His | Met | Asn | Gly | Tyr | Gly | Val | His | Ser | Phe | Arg | Phe |
|     |     |     |     | 245 |     |     |     |     | 250 |     |     |     |     | 255 |     |
| Val | Ala | Ala | Asn | Gly | Thr | Ser | Lys | Val | Val | Arg | Thr | Pro | Trp | Lys | Ser |
|     |     |     |     | 260 |     |     |     |     | 265 |     |     |     |     | 270 |     |
| Gln | Gln | Gly | Val | Ala | Ser | Leu | Val | Trp | Asp | Glu | Ala | Gln | Ala | Ala | Ala |
|     |     |     | 275 |     |     |     |     | 280 |     |     |     |     | 285 |     |     |
| Gly | Lys | Asn | Ser | Asp | Tyr | His | Arg | Gln | Asp | Leu | Tyr | Asn | Ala | Met | Pro |
|     |     | 290 |     |     |     |     | 295 |     |     |     |     | 300 |     |     |     |
| Asn | Gly | His | Tyr | Pro | Lys | Tyr | Glu | Leu | Gln | Ala | Gln | Ile | Met | Asp | Glu |
| 305 |     |     |     |     | 310 |     |     |     |     | 315 |     |     |     |     | 320 |
| Ala | Asp | Met | Leu | Arg | Phe | Gly | Phe | Asp | Leu | Leu | Asp | Pro | Thr | Lys | Leu |
|     |     |     |     | 325 |     |     |     |     | 330 |     |     |     |     | 335 |     |
| Val | Pro | Glu | Glu | Val | Val | Pro | Tyr | Thr | Pro | Leu | Gly | Met | Met | Glu | Leu |
|     |     |     |     | 340 |     |     |     |     | 345 |     |     |     |     | 350 |     |
| Asn | Ala | Asn | Pro | Thr | Asn | Tyr | Phe | Ala | Glu | Val | Glu | Gln | Ala | Gly | Phe |
|     |     | 355 |     |     |     |     | 360 |     |     |     |     | 365 |     |     |     |
| Gln | Pro | Gly | His | Val | Val | Pro | Gly | Ile | Asp | Phe | Thr | Asp | Asp | Pro | Leu |
|     |     | 370 |     |     |     |     | 375 |     |     |     |     | 380 |     |     |     |
| Leu | Gln | Gly | Arg | Leu | Phe | Ser | Tyr | Leu | Asp | Thr | Gln | Leu | Thr | Arg | His |
| 385 |     |     |     |     | 390 |     |     |     |     | 395 |     |     |     |     | 400 |
| Gly | Gly | Pro | Asn | Phe | Glu | Gln | Ile | Pro | Val | Asn | Arg | Pro | Arg | Lys | Pro |
|     |     |     |     | 405 |     |     |     |     | 410 |     |     |     |     | 415 |     |
| Val | His | Asn | Asn | Asn | Arg | Asp | Gly | Phe | Gly | Gln | Gln | Gln | Ile | Pro | Thr |
|     |     |     |     | 420 |     |     |     |     | 425 |     |     |     |     | 430 |     |
| Asn | Asn | Trp | Ala | Tyr | Thr | Pro | Asn | Ser | Met | Ser | Asn | Gly | Tyr | Pro | Met |
|     |     |     | 435 |     |     |     |     | 440 |     |     |     |     | 445 |     |     |
| Gln | Ala | Asn | Gln | Thr | Gln | Gly | His | Gly | Phe | Phe | Thr | Ala | Pro | Tyr | Arg |
|     |     | 450 |     |     |     |     | 455 |     |     |     |     | 460 |     |     |     |
| Tyr | Ala | Ser | Gly | His | Leu | Val | Arg | Gln | Thr | Ser | Pro | Thr | Phe | Asn | Asp |
| 465 |     |     |     |     | 470 |     |     |     |     | 475 |     |     |     |     | 480 |
| His | Trp | Ser | Gln | Pro | Ala | Met | Phe | Trp | Asn | Ser | Leu | Ile | Pro | Ala | Glu |
|     |     |     |     | 485 |     |     |     |     | 490 |     |     |     |     | 495 |     |
| Gln | Gln | Met | Val | Val | Asn | Ala | Ile | Val | Phe | Glu | Asn | Ser | Lys | Val | Asn |
|     |     |     | 500 |     |     |     |     | 505 |     |     |     |     | 510 |     |     |
| Ser | Pro | His | Val | Arg | Lys | Asn | Val | Val | Asn | Gln | Leu | Asn | Met | Val | Asn |
|     |     | 515 |     |     |     |     | 520 |     |     |     |     | 525 |     |     |     |
| Asn | Asn | Leu | Ala | Val | Arg | Val | Ala | Arg | Gly | Leu | Gly | Leu | Asp | Glu | Pro |
| 530 |     |     |     |     | 535 |     |     |     |     | 540 |     |     |     |     |     |

| Ser | Pro | Asn | Pro | Thr | Tyr | Tyr | Thr | Ser | Asn | Lys | Thr | Ser | Asn | Val | Gly |
| 545 |     |     |     |     | 550 |     |     |     |     | 555 |     |     |     |     | 560 |

| Thr | Phe | Gly | Lys | Pro | Leu | Leu | Ser | Ile | Glu | Gly | Leu | Gln | Val | Gly | Phe |
|     |     |     |     | 565 |     |     |     |     | 570 |     |     |     |     | 575 |     |

| Leu | Ala | Ser | Asn | Ser | His | Pro | Glu | Ser | Ile | Lys | Gln | Gly | Gln | Ala | Met |
|     |     |     | 580 |     |     |     |     | 585 |     |     |     |     | 590 |     |     |

| Ala | Ala | Gln | Phe | Ser | Ala | Ala | Gly | Val | Asp | Leu | Asn | Ile | Val | Thr | Glu |
|     |     |     | 595 |     |     |     |     | 600 |     |     |     |     | 605 |     |     |

| Ala | Tyr | Ala | Asp | Gly | Val | Asn | Thr | Thr | Tyr | Ala | Leu | Ser | Asp | Ala | Ile |
|     | 610 |     |     |     |     | 615 |     |     |     |     | 620 |     |     |     |     |

| Asp | Phe | Asp | Ala | Leu | Ile | Ile | Ala | Asp | Gly | Val | Gln | Ser | Leu | Phe | Ala |
| 625 |     |     |     |     | 630 |     |     |     |     | 635 |     |     |     |     | 640 |

| Ser | Pro | Ala | Leu | Ala | Asn | Gln | Met | Asn | Ser | Thr | Ala | Thr | Ser | Thr | Leu |
|     |     |     |     | 645 |     |     |     |     | 650 |     |     |     |     | 655 |     |

| Tyr | Pro | Pro | Ala | Arg | Pro | Phe | Gln | Ile | Leu | Val | Asp | Ser | Phe | Arg | Tyr |
|     |     |     | 660 |     |     |     |     | 665 |     |     |     |     | 670 |     |     |

| Gly | Lys | Pro | Val | Ala | Ala | Val | Gly | Ser | Gly | Ser | Val | Ala | Leu | Lys | Asn |
|     |     | 675 |     |     |     |     | 680 |     |     |     |     | 685 |     |     |     |

| Ala | Gly | Ile | Asp | Ser | Ser | Arg | Ser | Gly | Val | Tyr | Thr | Gly | Ser | Ser | Glu |
|     | 690 |     |     |     |     | 695 |     |     |     |     | 700 |     |     |     |     |

| Thr | Thr | Glu | Lys | Ile | Ala | Lys | Glu | Val | Leu | Glu | Gly | Leu | Tyr | Thr | Phe |
| 705 |     |     |     | 710 |     |     |     |     | 715 |     |     |     |     | 720 |     |

| Arg | Phe | Val | Asp | Arg | Phe | Ala | Leu | Asp | Glu |
|     |     |     |     | 725 |     |     |     | 730 |     |

( 2 ) INFORMATION FOR SEQ ID NO:6:

( i ) SEQUENCE CHARACTERISTICS:
        ( A ) LENGTH: 8533 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:6:

| GCGGCCGCCT | CGAGGATTGT | CTGAACATTG | ACATTCGGCG | CCCAGCGAAC | CCCAACTGCG | 60 |
| GACGCGAATG | CCCGTGCTGG | TCTCGGATCT | TTGGCGGAGG | CTTTGAACTT | GGTTCAAAGG | 120 |
| CCATGTATGA | CGGCACAACG | ATGGTATCAT | CGTCGATAGA | CAAGAATATG | CCTATCGTGT | 180 |
| TTGTAGCGAT | GAACTATCGC | GTAGGGGGCT | TCGGGTTTCT | GCCCGGAAAG | GAGATTCTGG | 240 |
| AGGACGGGTC | CGCCAACTTA | GGTCTTTGAC | CAAGCCTTGC | CCTAGTGGGT | GGCCGACAAC | 300 |
| ATCGAGGCGT | TGGTGGAGA  | CCAGACAAGG | TGACAATCTG | GGGAGAATCA | GCAGGGGCTA | 360 |
| TTTCTGTCTT | GATCAGATGA | TCTGTACGAC | GGAAACATCG | CTTACAAGGA | CAAGCCCTTG | 420 |
| TTTCGGGAGC | CATCATGGAC | TCCGGTATGT | GTTCCCGCAG | ACCCTGTCGA | CGGGGTCAAG | 480 |
| GGATCAGCAA | GTATATGATG | CGGTTGTGGA | CTCTGCAGGC | TGTTCCTCTT | CCAACGACAC | 540 |
| CCTGGCTTGT | CTGCGTGAGC | TAGACTACAC | CGACTATCTC | AATGCGGCAA | ACTCGTGCCG | 600 |
| GGGATCCTAG | GTTATCACCG | TGGCGCTATC | ATATGTGCCT | CGACCAGACG | GGACGGCATT | 660 |
| TGTCGGCGTC | GCCAGATTTT | GGGTAAAGCA | GGAAGTATG  | CGCGGGTCCC | ATTCATCGTG | 720 |
| GGCGACCAAG | AGGATGAGGG | GACCTTGTTC | GCCTTGTTTC | AGTCCTTACG | ACGATCGACG | 780 |
| AGGTAGTCGA | CTATCTGGGC | ACCTACTTCT | TCTATGACGC | TAGCCAGGAG | CAGCTTGAAG | 840 |
| AATTAGTGGC | CCTGTACCCA | GACACCACCA | CATATGGGTC | TCCCTTCAGG | ACGGGCAGGC | 900 |
| CAACAACTGG | TATCCGCAAT | TTAAGCGATT | GGCCGCCATT | CTCGGCGACT | TGGTCTTCAC | 960 |

| | | | | | |
|---|---|---|---|---|---|
| CATTACCCGG | CGGCATTCCT | GTCATATGCA | GAGGAGCTCT | CCCCTGACCT | CCCGAAATGG | 1020 |
| TCGTACCTGG | CGACCTATGA | CTATGGCAGC | CAATTCTGGG | GACCTTCCAT | GGAAGTGACC | 1080 |
| TGCTGCAGGT | GTTCTATGGG | ATCAAGCCGA | ACTATGCAGC | GAGTTCCAGC | CACACGTATT | 1140 |
| ATCTGAGTTT | TGTATACACG | CTGGATCCGA | ACTCCAATCG | GGGGAGTAC | ATGGAATGGC | 1200 |
| CCCAGTGGCA | GCCGACAGTT | GATGAATTTC | GGAGCGAACA | GCAGTCTCCT | TACGGATGAT | 1260 |
| TTCCGCAACG | GGACATATGA | GTTCATCCTG | CAGAATACCG | CGGCGTTCCA | CATCTGATGC | 1320 |
| CATTCGGGAG | GGGTCCGGAG | GTCAGGGACT | AGCCTTATGA | ACGTAATGAT | GGAAGTGTCT | 1380 |
| GGCCTCGGCA | AAGGATATAT | AGGGTCATAA | TAAGTAGTAC | TAGTTATATT | AATGGAAGGG | 1440 |
| TATATACCAC | GCGTTGGACC | TTGGGACCTG | CATTATAGCT | TCCCGTTAGG | TATAATTACC | 1500 |
| GTTGTTATAG | CAGCCAATCA | AGCCACCACG | CTCGACCGGG | GACGGCGAA | TCCCGGGAA | 1560 |
| TTGAAATAAA | TTGCAATTCA | GGTCAATGCG | GCCAGCGATT | GGACACATCT | CCAAGGCACA | 1620 |
| GGGCCATTCT | GCAGTGCCGG | GGATTCAGTG | CATTCCCCG | GGCCGGGCCC | GACACGCGAT | 1680 |
| AGGCTGGTTC | TTCCACACCA | CCGGAGATTC | GTCGTTCTGA | AGAGCTGAAG | TGGCGAGATG | 1740 |
| GTCTCTGCAG | GAATTCAAGC | TAGATGCTAA | GCGATATTGC | ATGGCAATAT | GTGTTGATGC | 1800 |
| ATGTGCTTCT | TCCTTCAGCT | TCCCCTCGTG | CAGATGAAGG | TTTGGCTATA | AATTGAAGTG | 1860 |
| GTTGGTCGGG | GGTTCCGTGA | GGGGCTGAAG | TGCTTCCTCC | CTTTTAGACG | CAACTGAGAG | 1920 |
| CCTGAGCTTC | ATCCCCAGCA | TCATTAGATC | TCAGCAATGC | GTCATTTCTG | GCTTTTGCCA | 1980 |
| GCTGTTGCTG | GTATCGCTGG | GGCTCAATGC | CCCTACCTGT | CGGGTGAAAT | GAGTTTCACC | 2040 |
| CAGGAGCAGG | ACAATGCTGG | CGATACCATT | GAGGTCACGG | AGCAGCCCAT | TGACAACACC | 2100 |
| CTGTATGTCA | ATGACACCGG | TAGCTACATG | ACTACCGACT | TTGGCACTCC | GATCTCCGAC | 2160 |
| CAGACCAGTC | TCAAGGCCGG | GCCCCGTGGT | CCTACCCTGT | TGGAGGACTT | TATCTTCCGT | 2220 |
| CAGAAGCTTC | AGCGGTTCGA | CCATGAGCGT | GTAAGTACAG | TAACTGCTGC | GGTGTGTAGT | 2280 |
| AACAATAAAT | TGACCCAGTG | GTTTTCAATT | AGGTCCCCGA | GCGCGTCGTC | CACGCCCGTG | 2340 |
| GTGCCGGTGC | ATATGGTACT | TTCAAATCCT | ACGCCGACTG | GTCGAACGTC | ACGGCTGCCG | 2400 |
| ATTTCTTGAG | TGCCAACGAT | AAGGAGACCC | CTATGTTCTG | TCGCTTCTCT | ACTGTGGTCG | 2460 |
| GTTTCCGTGG | TAGTGTTGAC | ACTGCGCGTG | ATGTTACGG | TCACGCTTGT | CGGTTCTACA | 2520 |
| CTGACGAGGG | TAACTATGGT | ATCTTGATAT | GGTCACCCAA | CAATAATTCA | ATACATGCTA | 2580 |
| ACAGATATGT | CTCTACTAGA | CATCGTCGGT | ATCAATTTCG | CCCCCTTCTT | CATCCAGGAC | 2640 |
| GCCATCCAGT | TCCCCGATCT | TGTCCACGCC | ATCAAGCCCA | TGCCCAACAA | TGAGATCCCC | 2700 |
| CAGGCCGCTA | CTGCACACAC | TTCCGCTTGG | GACTTCTTCA | GCCAGCAGAG | CACTGCCCTC | 2760 |
| CACAGTGCCT | TGTGGCTGAT | GTCTGGTAAC | GGTATTCCTC | GTTCTTTCCG | CCACATGAAC | 2820 |
| GGCTACGGAG | TCCACAGCTT | CCGCTTCGTC | GCTGCCAATG | GCACTTCCAA | GGTGGTGCGA | 2880 |
| ACACCTTGGA | AGTCCCAACA | GGGTGTTGCC | AGTCTGGTGT | GGGATGAAGC | TCAGGCCGCT | 2940 |
| GCTGGTAAGA | ACAGTGACTA | CCACCGCCAG | GATCTGTACA | ATGCGATGCC | CAATGGCCAC | 3000 |
| TACCCGAAAT | ACGAGGTCAG | CCAATCCCTT | GATGTCTATC | GATAGAGCCT | TTTGCTGACA | 3060 |
| ATCCCCTAGC | TCCAAGCCCA | GATCATGGAT | GAGGCTGACA | TGCTTCGTTT | CGGCTTCGAC | 3120 |
| CTTCTGGATC | CCACCAAGTT | GGTCCCCGAG | GAGGTTGTCC | CTTACACTCC | TCTCGGAATG | 3180 |
| ATGGAGCTCA | ATGCCAACCC | CACCAACTAC | TTTGCTGAAG | TTGAACAGGC | TGGTGTATGT | 3240 |
| ATTCCCCATT | CATCAAATGC | CAGACATAAT | CTAACTTCTG | CAGTTCCAAC | CCGGTCACGT | 3300 |
| CGTTCCTGGC | ATTGACTTCA | CCGACGACCC | CCTGCTGCAA | GGCCGTCTCT | TCTCCTACCT | 3360 |
| CGACACTCAG | TTGACCCGTC | ACGGCGGTCC | CAACTTCGAG | CAAATCCCCG | TCAACCGTCC | 3420 |

| | | | | | |
|---|---|---|---|---|---|
| TCGCAAGCCC | GTTCACAACA | ACAACCGTGA | CGGCTTCGGC | CAGCAGCAGA | TCCCCACCAA 3480 |
| CAACTGGGCC | TACACCCCCA | ACAGCATGAG | CAACGGTTAC | CCCATGCAAG | CCAACCAGAC 3540 |
| CCAGGGTCAT | GGTTTCTTCA | CCGCGCCCTA | CCGCTACGCT | TCCGGCCATC | TCGTCCGCCA 3600 |
| GACCAGCCCG | ACCTTCAATG | ACCACTGGTC | CCAGCCCGCC | ATGTTCTGGA | ACTCTCTGAT 3660 |
| CCCCGCTGAG | CAGCAGATGG | TTGTCAACGC | CATTGTCTTT | GAGAACTCCA | AGGTTAACAG 3720 |
| CCCCCACGTT | CGGAAGAACG | TTGTCAACCA | GCTGAACATG | GTCAACAACA | ACCTCGCCGT 3780 |
| CCGTGTCGCT | CGTGGTCTTG | GTCTCGATGA | GCCCTCCCCC | AACCCGACTT | ACTACACCTC 3840 |
| CAACAAGACC | TCCAACGTCG | GTACCTTCGG | CAAGCCCCTC | CTCAGCATCG | AGGGTCTGCA 3900 |
| GGTCGGCTTC | CTGGCCTCGA | ACTCCCACCC | CGAATCCATC | AAGCAGGGCC | AGGCCATGGC 3960 |
| CGCGCAGTTC | TCTGCCGCTG | GCGTCGACCT | GAACATTGTC | ACCGAGGCCT | ACGCCGATGG 4020 |
| TGTCAACACC | ACCTACGCCC | TGTCTGATGC | CATCGACTTT | GACGCCCTCA | TCATCGCCGA 4080 |
| TGGTGTGCAG | AGCCTCTTCG | CCTCCCCCGC | TCTCGCTAAC | CAGATGAACT | CTACCGCCAC 4140 |
| CTCTACTCTC | TACCCTCCTG | CCAGACCTTT | CCAGATCCTG | GTCGATTCTT | TCAGGTACGG 4200 |
| TAAGCCCGTG | GCTGCTGTCG | GCAGTGGCAG | TGTTGCGCTC | AAGAACGCTG | GTATTGATTC 4260 |
| CTCCGCTCT | GGTGTGTACA | CTGGCTCGAG | CGAGACGACG | GAGAAGATCG | CCAAGGAGGT 4320 |
| CTTGGAGGGA | CTCTACACTT | TCCGTTTTGT | GGACCGGTTT | GCGCTGGATG | AGTAAGGGTA 4380 |
| TCACGTTTGT | ACTTGTACTC | ACGTTCATCG | TTTGTGATGA | TACATTGATT | GATCGATAGT 4440 |
| CTAGAGTCGA | CCGCGACGGT | GACCGACACC | TGGCGGTAGA | CTATTTATTC | CTGTTGATAT 4500 |
| GAAGGATGAG | CATGAGGGTA | ATTGCTCATA | TAATCATGTA | TGTAGTGGAT | GTGCATAAGA 4560 |
| GCAACGAAAT | GGAAGCCTGA | TCATGTGATT | GTATTGCGAC | CGACGGAAAT | TGAGGATATG 4620 |
| CGGAGATACG | GACAGTGCCA | GAGCCATTGT | CTTCACGTAA | AGTACCAGAC | GGTCCCTGAT 4680 |
| TTCTTCTTGC | ACATAGCATT | AGGCAATTGA | CATGTTGTCG | CTCTACTGAT | ATCACTGTCC 4740 |
| CTCAAAGCAT | AGCCATGAGC | TCATCTTAGA | TCCAAGCACG | TAATTCCATA | GCCGAGGTCC 4800 |
| ACAGTGGAGC | AACAGCAGCA | TCCATCATTG | CTTCTCCCCC | AGGGGCCTCT | TAGCGACTAA 4860 |
| ACCTGGAGTA | TGTCTCAACC | AGCCAATGAA | TCGTCTTCGC | TTCAATGTCC | TTGACACTTC 4920 |
| TGAGGGGTC | CCCATCCCTC | AATGCTAATT | CAAATATAG | CCGAGATGCA | TGGTGGAGTC 4980 |
| CAAAGTAGAC | AGTATTGCCG | GAATGACGGG | GCCAGTTGCG | CCGAGGTCAT | GGCCGGCTG 5040 |
| TGATGCCATC | TGCCACTAAA | TCCGATCATT | GATCCACCGC | CACGAGGGC | CGTCTTTGCT 5100 |
| TTTGCGCTGC | GTCCAGGTTC | ACACATCTCT | CTCTCTGCAG | CTCCAGACTG | ACCAGACTAT 5160 |
| TCTACTTACT | GGTCTGATCG | GCTCCATCAG | AGCTATGGCG | TTATCCCGTG | CCGTTGCTGC 5220 |
| GCCATCGCTA | TCTTGATCGC | GAGCTCGAAC | TCACTTCTTG | TTTTAATAGT | TGTTCTCGGT 5280 |
| GACTGAGTGT | CGGTGAGTGA | CAGACCACAA | CACCATTGTT | GCAGGGGTA | AATTTATTCA 5340 |
| ATTCAGGAAT | TGGATTGTTC | GTCCCGCCAT | GATGTTCTTG | CCGGCTTTGT | TGGCCCTGTT 5400 |
| TGTCGGATGC | GACGCCCTCG | CTGTGCAGCA | GGCAGGTACT | GCTGGATGAT | GAGCCGTCGG 5460 |
| TCTCCGCGCG | CAAGCCTAAC | TTCCTCTTCA | TTCTTACGGA | TGATCAGGAT | CTGCAGATCG 5520 |
| AATTCCACCG | GCGTATATGC | CGTATACACA | GGCGAGAATC | AAGGAGAAGG | GTACTGAGTT 5580 |
| TTGAATCATT | TGTTACTACT | GGCTCTGTGC | TGTCCGTCGC | GCGTGAGTCT | TTGGACGGAA 5640 |
| GACAGGCTCA | TAATACTAAT | GTGACGGATG | TGAACCCGCC | TTATGGTATG | AATACCTCTC 5700 |
| AGATCGGTCA | TGTTTCTTCG | GTGTAAAATT | GCTAATGCAG | CATAGGCGGA | TACCCCAAGT 5760 |
| TCGTCGCCCA | AGGCTTCAAC | GAAAACTTCC | TCCCCGTTTG | GCTGCAGTCC | GCCGGTTACA 5820 |
| ATACCTTCTA | CACGGGGAAA | CTGTTCAACT | GCCACAGCGT | CGCTACCTAT | AATGCACCGT 5880 |

| | | | | | | |
|---|---|---|---|---|---|---|
| TTGTGAACGG | CTTCAATGGC | TCTGATTTCC | TCCTCGATCC | CCACACCTAT | TCCTACTGGA | 5940 |
| ACGCGACGTA | CCAACGAAAC | CATGAGCCTC | CGCGGAGCTA | CGAGGGACAA | TACACAACGG | 6000 |
| ATGTGATGCG | GGAGAAGGCA | TCGGGGTTGT | TGGCAGATGC | GCTGGACAGG | ACGCGCCGTT | 6060 |
| CTTCTGACGG | TGCCTATCCG | CCGCACACGA | ACATCGATAA | GCTTATCACC | GTCCCTTATC | 6120 |
| AGCCACCCGT | CGCCATTTGC | TCTACGCAAG | AGTTACAGGA | CTAAGTACTT | CGCAGCCTGC | 6180 |
| TTATCTGCAT | CAAATCGTCG | TACCGCATTA | ATCCCGTGCC | ACCCTATAAT | AGCCTGCAGG | 6240 |
| ATCAATACCG | TTTTGACATC | CGATGCCGCA | GTCTGACTAC | CCGTGCTCGA | CATTAGTTTG | 6300 |
| TATGCGTATC | GTAGCGGCAA | GTTGCATTTC | TATATCATTC | ATAACCATCA | AAACTTTTTT | 6360 |
| CCTCATTTTA | TAGTATTAGT | TTCCGCCGAC | ACGGGCCAGG | TACGCCTCCC | AACCTTCCTT | 6420 |
| CTGGTACTGT | TGCGCAGCCT | GCACCGGGTC | CGGCGCGGCG | TAGATACCGC | GACCCGCGAT | 6480 |
| AATGAAGTCA | GCACCCCGAC | CGATAGCCGA | TGCGGGAGTC | TGGTACTGCT | GACCGAGCTT | 6540 |
| ATCTCCCTTG | GACGAAATGT | TCACACCAGT | CGTGAAGACC | ACAAAGTCCT | CCTCATCCGA | 6600 |
| AGGAGAGCTG | ACTTCCGACT | GCACCTCACC | CAACGAGCGG | GTCGACACAA | ATCCCATGAC | 6660 |
| GAAGTTCTTG | TATTTCCGGG | CATAATCAAC | CGAAGAAGTA | GTGTACTGGC | CGGTGGCCAA | 6720 |
| GGAACCCTTA | GAGGTCATTT | CCGCCAAGAT | CAACAGACCA | CGTTCGGGGC | CGTAGGAGAA | 6780 |
| GTCCGGTGCA | GACGCCGTCT | GAGCGAGAGC | CTCGACGATA | CCCTCGCCAG | GCAGGATGCT | 6840 |
| GCAGTTGATG | ATATGGGCCC | ATTCTGAGAT | GCGGAGGGTA | CCACGGTGGT | ATTGCTTCTG | 6900 |
| GACAGTGTTG | CCAATGTCGA | TGAATTTGCG | GTCCTCGAAG | ATGAGGAAGT | TGTGCTTCTG | 6960 |
| CGCAAGAGCC | TTGAGGCCCT | CAATGGTCTC | GTCGCTGAAG | TCAGAGAGGA | TATCGATGTG | 7020 |
| GGTTTTGATC | ACGGCGATGT | AGGGACCGAG | ACCTCAGTCC | GGTATCACCG | TTAATAAGTT | 7080 |
| TGTATGCAGC | ATAAACAGGC | AGAATGGCGG | GTCGGCCTAC | GGTCAGCAAG | ATCTAGTAGC | 7140 |
| TCCTTAGTGG | TGGTAACGTC | GGCAGAGACG | GTCACATTGG | TCTTCTTGGC | CTCAGCAATT | 7200 |
| TCGAACAGCC | GCTTGGCCAG | AGCATTGGGG | TGCTTGCTGG | CACGGGCAGT | GTAGGTCAAT | 7260 |
| TGCGACTTGG | AGGACATGGT | GTCGGTGGAG | GGGTTAATGC | GGGGATGAAA | GAGGCTTGTG | 7320 |
| CAATATGAGT | AGCTTGGAGT | TTCGACTGAT | AGGCCCTAAT | TGGTAGATCC | AGAGATGCGC | 7380 |
| AAATACTACC | GAATAATTTA | GCAGCGACTG | GCCCTTATAT | GAGGTGAACA | ATGCACATTC | 7440 |
| AATGTCGAGC | AAAAGAGGAG | CTCAGTAAAT | CATCGCGACC | CTCCACGCAC | CAGCCACATC | 7500 |
| GGGTGATTTC | GCCGCCTCCG | ACCGGAACCG | TGGGGTTCAG | CCACACCTGC | AAAGGCAGTT | 7560 |
| CCTTTCCATT | GAAGTTGCCA | CACCCAGGTT | CATTGGAGCT | CGTATTTTTC | CCTGCTGCAC | 7620 |
| ATGGGGAAAT | AGACCAGCTC | AATCAGAAAG | CCATTGTCAT | TCCCGACCCT | AGCAGTACGC | 7680 |
| ATAGTAAACG | CGTCGTGGAG | TAGTAATATA | CAAGTGAGAA | ATTTATTACA | TATAGCGTGG | 7740 |
| TATAGCCAAC | AGCGCCAATC | ACACCCGACG | GAAGTCAATC | CAAACTTTAA | AAGGTAGGGA | 7800 |
| AATCAACTCC | CTCGCGACTT | CCAAAAGAGG | TCAATCCCCA | AAGAGCTCCC | TGTGCAAGCA | 7860 |
| AGTAGAAGCT | GCCGTACAAC | CGGACCGACC | CCGGCTTGCC | GGAGTACACG | TATCCGTAAA | 7920 |
| GGAACAGTGA | GCGACCGAGA | ACCCAAATGC | TTCCAAGGCC | AGTTGCCAAC | TGGGGGTACT | 7980 |
| TCAATCCAGC | CACCAGGATG | AAGAGCATAG | TTTGGCTGGA | GTTCTCAAGG | AAGTTGGCAT | 8040 |
| GAGCGTGAGC | GAGTTAACTG | CTCAGCCTTG | GGCTGCACGA | TTGGAATGTA | TGTTAGCTCG | 8100 |
| AGGAATCTTG | TCCGTCTGAG | GTTGGTAGGT | TGGCTTACGT | TGTCTTGCAC | TGCACTACGG | 8160 |
| TCGCATAGCA | GTGAGGGTAG | GGGCAATCGG | CGTTCTTACG | GAGACGAGAC | ACGACGGCGC | 8220 |
| CATGGACGAA | GCTCAGGACG | GGGATGGCGC | CCAGAGCGAC | GGCAATGACA | GAGCTGCAGG | 8280 |
| ATGATTAGCA | TCAGACTATA | TGGGACCTAA | TGGCATTGTT | TGCAGGGATT | GTGGAATTGG | 8340 |

| CACATACCCG | TAGTTTTCAG | GGACGGTCAG | AGTAAGCATG | GTGAGATATT | AACTTGTAGT | 8400 |
| GTTTTCAATT | TGAATCTGCT | ATGACTAGGC | GGTATTGGGA | AGTCTAGAAG | AAGCCGAAAG | 8460 |
| TGATTCAATT | TATATAATCG | GCGATTGATG | GGGCGCAAGA | GCGCGATGCG | GATCCGGCCA | 8520 |
| AAACCGTTTA | AAC | | | | | 8533 |

(2) INFORMATION FOR SEQ ID NO:7:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

ATGTTCTGGA ACAGCCTGAT CCCCGCCGAG CAGCAGATG    39

(2) INFORMATION FOR SEQ ID NO:8:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

ATGTTCTGGA ACTCCCTGAT CCCCGCCGAG CAGCAGATG    39

(2) INFORMATION FOR SEQ ID NO:9:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

ATGTTCTGGA ACAGCTTGAT CCCCGCCGAG CAGCAGATG    39

What is claimed is:

1. An isolated and purified gene sequence encoding catalase-R from *Aspergillus niger* having the amino acid sequence consisting essentially of SEQ ID NO:5.

2. An isolated and purified gene sequence encoding catalase-R from *Aspergillus niger* consisting essentially of the sequence in SEQ ID NO:4.

* * * * *